(12) United States Patent
Eickbush et al.

(10) Patent No.: US 7,153,672 B1
(45) Date of Patent: Dec. 26, 2006

(54) METHOD OF PERFORMING REVERSE TRANSCRIPTION REACTION USING REVERSE TRANSCRIPTASE ENCODED BY NON-LTR RETROTRANSPOSABLE ELEMENT

(75) Inventors: Thomas H. Eickbush, Penfield, NY (US); Arkadiusz Bibillo, Rochester, NY (US)

(73) Assignee: University of Rochester, Rochester, NY (US)

( * ) Notice: Subject to any disclaimer, the term of this patent is extended or adjusted under 35 U.S.C. 154(b) by 461 days.

(21) Appl. No.: 10/362,703

(22) PCT Filed: Aug. 30, 2001

(86) PCT No.: PCT/US01/27125

§ 371 (c)(1),
(2), (4) Date: Feb. 25, 2003

(87) PCT Pub. No.: WO02/18591

PCT Pub. Date: Mar. 7, 2002

Related U.S. Application Data

(60) Provisional application No. 60/229,075, filed on Aug. 30, 2000.

(51) Int. Cl.
*C12P 19/34* (2006.01)
*C12N 15/64* (2006.01)
*C07H 21/04* (2006.01)
*C07K 14/00* (2006.01)
*C07K 14/435* (2006.01)

(52) U.S. Cl. .................. 435/91.2; 435/6; 435/91.1; 435/91.5; 435/91.51

(58) Field of Classification Search .................. None
See application file for complete search history.

(56) References Cited

U.S. PATENT DOCUMENTS 5,244,797 A * 9/1993 Kotewicz et al. ........... 435/194
5,767,064 A   6/1998 Sims et al.
5,889,145 A   3/1999 Rood

OTHER PUBLICATIONS

Bibillo et al., J. Mol. Biol., 2002, vol. 316, pp. 459-473.*
Moran et al., Genetica, 1999, vol. 107, pp. 39-51.*
Gabriel et al., PNAS, 1991, vol. 88, pp. 9794-9798.*
Burke et al., "The Site-Specific Ribosomal Insertion Element Type II of *Bombyx mori* (R2Bm) Contains the Coding Sequence for a Reverse Transcriptase-Like Enzyme," *Mol. Cell Biol.* 7(6):2221-2230 (1987).
Xiong et al., "Functional Expression of a Sequence-Specific Endonuclease Encoded by the Retrotransposon R2Bm," *Cell* 55:235-246 (1988).
Luan et al., "Reverse Transcription of R2Bm RNA is Primed by a Nick at the Chromosomal Target Site: A Mechanism for Non-LTR Retrotransposition," *Cell* 72:595-605 (1993).
Luan et al., "RNA Template Requirements for Target DNA-Primed Reverse Transcription by the R2 Retrotransposable Element," *Mol. Cell Biol.* 15(7):3882-3891 (1995).
Luan et al., "Downstream 28S Gene Sequences on the RNA Template Affect the Choice of Primer and the Accuracy of Initation by the R2 Reverse Transcriptase," *Mol. Cell Biol.* 16(9):4726-4734 (1996).
Yang et al., "RNA-Induced Changes in the Activity of the Endonuclease Encoded by the R2 Retrotransposable Element," *Mol. Cell Biol.* 18(6):3455-3465 (1998).
Yang et al., "Identification of the Endonuclease Domain Encoded by R2 and Other Site-Specific, Non-Long Terminal Repeat Retrotransposable Elements," *Proc. Natl. Acad. Sci. USA* 96:7847-7852 (1999).
Burke et al., "The Domain Structure and Retrotransposition Mechanism of R2 Elements Are Conserved Throughout Arthropods," *Mol. Biol. Evol.* 16(4):502-511 (1999).
Eickbush et al., "Site-Specific Non-LTR Retrotransposable Elements," Poster presented at UCLA Keystone Meeting, Taos, NM (Jan. 29, 2000) (abstract).
Bibillo et al., "The R2 Protein Can Switch to the 3' End of Another Template to Continue Reverse Transcription," Poster presented at UCLA Keystone Meeting, Taos, NM (Jan. 29, 2000) (abstract).
Eickbush et al., "Integration of *Bombyx mori* R2 Sequences into the 28S Ribosomal RNA Genes of *Drosophila melanogaster*," *Mol. Cell Biol.* 20(1):213-223 (2000).
Eickbush et al., "Retrotransposable Elements That Specifically Insert into the 28S Ribosomal RNA Genes: Their Distribution in Insects and Use for Genetic Transformation," XX International Congress of Entomology, Firenze, Italy, (Aug. 25-31, 1996) (abstract).
Chabossier et al., "Retrotransposition of the *I* Factor, a Non-Long Terminal Repeat Retrotransposon of *Drosophila*, Generates Tandem Repeats at the 3' End," *Nucleic Acids Research* 28(13):2467-2472 (2000).
Mathews et al., "Secondary Structure Model of the RNA Recognized by the Reverse Transcriptase from the R2 Retrotransposable Element," *RNA* 3:1-16 (1997).

* cited by examiner

*Primary Examiner*—David Guzo
(74) *Attorney, Agent, or Firm*—Nixon Peabody LLP

(57) ABSTRACT

The present invention relates to a method of preparing a cDNA molecule which includes: contacting an RNA molecule, in the presence of dNTPs, with a non-LTR retrotransposon protein or polypeptide having reverse transcriptase activity under conditions effective for production of a cDNA molecule complementary to the RNA molecule, the contacting being carried out in the absence of a target DNA molecule of the non-LTR retrotransposon protein or polypeptide; and isolating the cDNA molecule. The preferred non-LTR retrotransposon protein or polypeptide is an R2 protein or polypeptide.

32 Claims, 19 Drawing Sheets

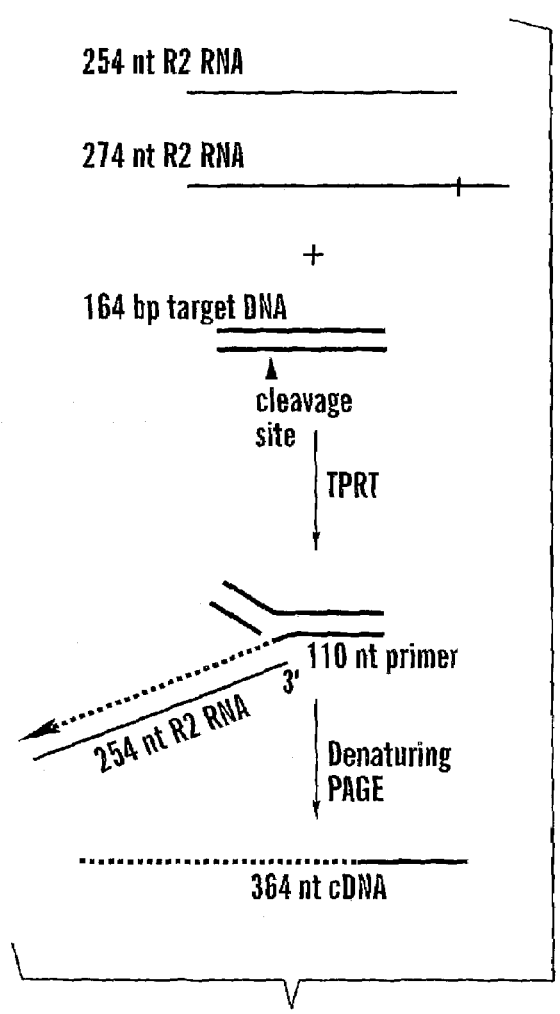
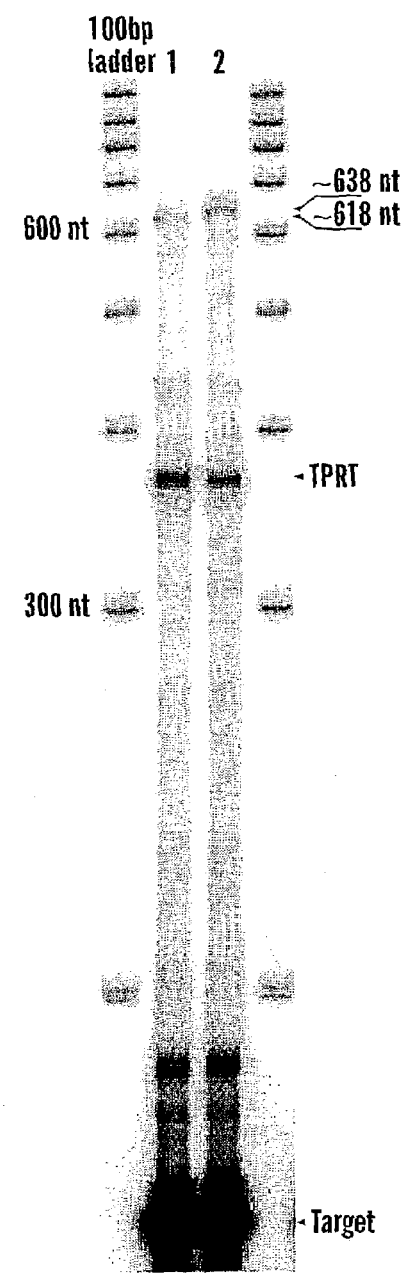
FIG. 1A
FIG. 1B

METHOD OF PERFORMING REVERSE TRANSCRIPTION REACTION USING REVERSE TRANSCRIPTASE ENCODED BY NON-LTR RETROTRANSPOSABLE ELEMENT

This application claims the benefit of U.S. Provisional Patent Application Ser. No. 60/229,075 to Eickbush et al., filed Aug. 30, 2000, which is hereby incorporated by reference in its entirety.

This invention was made, at least in part, utilizing funding received from the National Institutes of Health grant GM42790. The U.S. government may have certain rights in this invention.

FIELD OF THE INVENTION

The present invention relates generally to the preparation of nucleic acid molecules using a protein or polypeptide having reverse transcriptase activity, particularly proteins or polypeptides which have reverse transcriptase activity and are encoded by a class of non-long terminal repeat ("non-LTR") retrotransposable elements.

BACKGROUND OF THE INVENTION

Reverse transcriptases, enzymes that catalyze RNA-dependent DNA synthesis, have been used as a component of transcription-based amplification systems. These systems amplify RNA and DNA target sequences up to 1 trillion fold. Exemplary systems are disclosed in PCT Patent Application WO 89/01050 to Burg et al.; PCT Patent Application WO 88/10315 to Gingeras et al.; European Patent Application 0 329 822 to Davey and Malek; European Patent Application 0 373 960 to Gingeras et al.; PCT Patent Application WO 91/02814 to Malek and Davey; and European Patent Application 0 408 295 A2 to Kacian and Fultz. Others have also been described or are otherwise commercially available.

Some of the transcription-based amplification methods are exceptionally convenient since the amplification reaction according to these methods is isothermal. Thus, these systems are particularly suited for routine clinical laboratory use in diagnostic tests (i.e., pathogen detection, cancer detection, etc.). Reverse transcriptases are also employed as an initial step in some protocols when the polymerase chain reaction (PCR) is used to amplify an RNA target. See U.S. Pat. No. 5,130,238 to Malek et al.; and Mocharla et al., Gene 99:271–275 (1990). In such "RT-PCR" procedures, the reverse transcriptase is used to make an initial complementary DNA ("cDNA") copy of the RNA target, which is then amplified by successive rounds of DNA replication.

Reverse transcriptases were once believed to be enzymes unique to the replication of retroviruses (Baltimore, "RNA-dependent DNA Polymerase in Virions of RNA Tumor Viruses," Nature 226:1209–1211 (1970); Temin and Mizutani, "RNA-Directed DNA Polymerase in Virions of Rous Sarcoma Viruses," Nature 226:1211–1213 (1970)). Reverse transcriptases are now known to be encoded by a wide range of genetic elements in both eukaryotes and prokaryotes (Varmus, "Reverse Transcription," Sci. Amer. 257:56–66 (1987); Temin, "Retrons in Bacteria," Nature 339:254–255 (1989)).

Most commercially available reverse transcriptase, however, are retroviral in origin. The retroviral reverse transcriptases have three enzymatic activities: a RNA-directed DNA polymerase activity, a DNA-directed DNA polymerase activity, and an RNAse H activity (Verma, "The Reverse Transcriptase," Biochim. Biophys. Acta 473:1–38 (1977)). The latter activity specifically degrades RNA contained in an RNA:DNA duplex. Degradation of the RNA strand of RNA:DNA intermediates by RNAse H is an important component of some transcription-based amplification systems and is to be distinguished from unwanted degradation due to contaminating nucleases, which interferes with amplification. While retroviral-derived reverse transcriptases lacking RNAse H activity have been developed (U.S. Pat. No. 6,063,608 to Kotewicz et al.), it should be noted that retroviral transcriptases are typically characterized by several characteristics which limit their usefulness. These include: the necessity to use an primer that will anneal to the RNA template, the low processivity of the enzymes (i.e., the tendency to dissociate from the RNA before reaching the end), and the inability of the enzymes to transcribe through region of RNA secondary structure.

Eukaryotic genomes in particular are filled with mobile elements, retrotransposons, that use reverse transcriptase for replication. The reverse transcriptases encoded by non-LTR retrotransposons are highly divergent in sequence from the retroviral enzymes and utilize entirely different mechanisms to prime cDNA synthesis.

One of the most abundant classes of reverse transcriptase-encoding elements is the non-LTR retrotransposons (also called LINEs, retroposons and poly A-retrotransposons). Studies of the purified reverse transcriptase from the R2 element of the silkmoth, Bombyx mori, have provided insights into the mechanism of non-LTR retrotransposition (Luan et al., "Reverse Transcription of R2Bm RNA is Primed by a Nick at the Chromosomal Target Site: A Mechanism for non-LTR Retrotransposition," Cell 72:595–605 (1993)). R2 elements are specialized for insertion into the 28S ribosomal RNA (rRNA) genes found in the nucleoli of eukaryotic cells. The 120 kilodalton protein encoded by R2 has both reverse transcriptase and endonuclease activity. Based on in vitro studies of these two activities, R2 retrotransposition is a coupled DNA cleavage/reverse transcription reaction (Luan and Eickbush, "RNA Template Requirements for Target DNA-Primed Reverse Transcription by the R2 Retrotransposable Element," Mol. Cell. Biol. 15:3882–3891 (1995); Luan and Eickbush, "Downstream 28S Gene Sequences on the RNA Template Affect the Choice of Primer and the Accuracy of Initiation by the R2 Reverse Transcriptase," Mol. Cell. Biol. 16:4726–4734 (1996); Mathews et al., "Secondary Structure Model of the RNA Recognized by the Reverse Transcriptase from the R2 Retrotransposable Element," RNA 3:1–16 (1997); Yang and Eickbush, "RNA-induced Changes in the Activity of the Endonuclease Encoded by the R2 Retrotransposable Element," Mol. Cell. Biol. 18:3455–3465 (1998); and Yang et al., "Identification of the Endonuclease Domain Encoded by R2 and Other Site-specific, non-Long Terminal Repeat Retrotransposable Elements," Proc Natl. Acad. Sci. USA 96:7847–7852 (1999)) The 3' end generated by a first-stand cleavage (nick) of the DNA target site is used as primer for reverse transcription of the RNA template. This utilization of the DNA target to prime cDNA synthesis has been called target-primed reverse transcription ("TPRT"). Removal of the RNA template and synthesis of the second DNA strand does not occur in vitro and is likely to involve the cellular DNA repair and replication machinery. While much has been learned about the TPRT reaction, the activity of any non-LTR element reverse transcriptase has not been characterized in the absence of their DNA target site.

The present invention is directed to overcoming the above-identified limitations of RT reactions performed using previously identified retroviral reverse transcriptases as well as other deficiencies in the art.

SUMMARY OF THE INVENTION

One aspect of the present invention relates to a method of preparing a cDNA molecule which includes: contacting an RNA molecule, in the presence of dNTPs, with a non-LTR retrotransposon protein or polypeptide having reverse transcriptase activity under conditions effective for production of a cDNA molecule complementary to the RNA molecule, said contacting being carried out in the absence of a target DNA molecule of the non-LTR retrotransposon protein or polypeptide; and isolating the cDNA molecule.

A second aspect of the present invention relates to a method of amplifying a cDNA molecule which includes: preparing a single-stranded cDNA molecule according to the present invention, wherein the single-stranded cDNA molecule includes a region of interest; annealing a first primer to the single-stranded cDNA molecule at a position 3' of the region of interest; and extending the first primer to form a complementary DNA strand including a complement of the region of interest.

A third aspect of the present invention relates to a kit which can be used to prepare cDNA from RNA. The kit includes: a carrier device including one or more compartments adapted to receive one or more containers; and a first container which includes a non-LTR retrotransposon protein or polypeptide having reverse transcriptase activity. The kit may further include: one or more additional containers selected from the group-consisting of (i) a second container which includes a buffer, (ii) a third container which includes dNTPs, (iii) a fourth container which includes donor RNA having a known sequence, and (iv) a fifth container which includes acceptor RNA having a known sequence.

A fourth aspect of the present invention relates to a pool of cDNA molecules prepared according to the method of preparing a cDNA molecule according to the present invention.

As used herein, "non-LTR retrotransposon protein or polypeptide" refers to naturally occurring proteins encoded by non-LTR retrotransposons and polypeptide fragments thereof which possess reverse transcriptase activity, as well as proteins or polypeptides derived therefrom which contain one or more amino acid substitutions that either enhance the reverse transcriptase activity thereof or have no deleterious effect thereon. A preferred class of non-LTR retrotransposon proteins or polypeptides are R2 proteins or polypeptides. Thus, as used herein, "R2 protein or polypeptide" refers to naturally occurring proteins encoded by R2 elements and polypeptide fragments thereof which possess reverse transcriptase activity, as well as proteins or polypeptides derived therefrom which contain one or more amino acid substitutions that either enhance the reverse transcriptase activity thereof or have no deleterious effect thereon.

Applicants have surprisingly discovered that the protein encoded by the R2 element of *Bombyx mori*, which has reverse transcriptase activity, has several unusual properties in the absence of its DNA target. It was previously shown that the protein encoded by the R2 element of *Bombyx mori* required its DNA target to carry out TPRT of its own RNA (Luan et al., "Reverse Transcription of R2Bm RNA is Primed by a Nick at the Chromosomal Target Site: A Mechanism for Non-LTR Retrotransposition," *Cell* 72:595–605 (1993); Luan et al., "RNA Template Requirements for Target DNA-Primed Reverse Transcription by the R2 Retrotransposable Element," *Mol. Cell Biol.* 15(7):3882–3891 (1995); Luan et al., "Downstream 28S Gene Sequences on the RNA Template Affect the Choice of Primer and the Accuracy of Initiation by the R2 Reverse Transcriptase," *Mol. Cell Biol.* 16(9):4726–4734 (1996), each of which is hereby incorporated by reference in its entirety). Because the R2 element protein can function as a reverse transcriptase in the absence of its target DNA, this protein (as well as polypeptide fragments thereof) can be used to prepare cDNA in a reverse transcription procedure of the present invention, which can then be followed by conventional amplification procedures to expand the copy number of the transcribed cDNAs. The present invention provides a number of benefits previously unrealized with reverse transcription procedures performed, for example, using retroviral or retroviral-derived proteins having reverse transcriptase activity. These include: (i) elimination of the need for sequence-specific primers, since R2 proteins or polypeptides have an ability to use the 3' end of any RNA to prime cDNA synthesis; (ii) ability to combine cDNA copies from multiple RNA templates into a single cDNA strand, which is the result of the R2 protein or polypeptide propensity to jump between RNA templates in the absence of any sequence identity; and (iii) a propensity to completely or nearly completely copy the RNA template to form a population of cDNA molecules having a greater concentration of substantially full-length cDNAs (as compared to the population provided by retroviral or retroviral-derived proteins having reverse transcriptase activity).

BRIEF DESCRIPTION OF THE DRAWINGS

FIG. 1A–B illustrate a mechanism of DNA cleavage during a TPRT assay for the R2 protein. FIG. 1A shows a diagram of the nucleic acid templates and products of the reactions conducted in FIG. 1B. In FIG. 1A, gray lines represent RNA templates; black lines represent DNA target; and dotted lines represent cDNA product. The DNA substrate is a uniformly $^{32}$P-labeled 164 bp fragment. The two RNAs used as templates are either 254 nt in length, corresponding to the 3' untranslated region of the R2 element from *B. mori*, or 274 nt in length containing an extra 20 nt of the 28S gene sequence downstream of the R2 insertion site. The TPRT reaction is initiated by a cleavage of the lower (noncoding) strand of the target DNA. The free DNA 3' end released by this nick is used to prime reverse transcription starting at the 3' end of the 254 nt template, or 20 nt from the 3' end of the R2 sequence in the 274 nt template (see also diagram in FIG. 2). Thus, the TPRT product with both RNAs is ~364 nt cDNA, including a 110 nt fragment of lower target DNA strand and an ~254 nt reverse transcript of the RNA template. FIG. 1B is an image of an autoradiograph of the reaction products separated on a 33 cm 6% denaturing polyacrylamide gel. The reactions contain 5 ng of the R2 protein, 20 ng of target DNA and 150 ng of RNA. Lane 1, 254 nt R2 RNA; Lane 2, 274 nt R2 RNA. In addition to the ~364 nt TPRT product, both lanes contain larger cDNA products (~618 and 638 nt) that represent jumps to the end of a second RNA template.

FIG. 5A is an autoradiograph illustrating the reverse transcription of the 334 nt vector RNA in the absence of the DNA target site. All reactions were conducted with 300 ng of the 334 nt vector RNA in the presence of [α-$^{32}$P] dCTP. Lane 1, primer extension reaction in which 50 ng primer AB.23 (SEQ ID No: 33, Table I) was pre-annealed to the RNA template. The reverse transcription products were treated with 2 μg RNase A for 10 min at 37° C. before electrophoresis. Lane 2, reaction identical to that in lane 1, but no primer was annealed to the RNA template. Lane 3, reaction conditions identical to that in lane 2 (no DNA primer), but the reaction products were not treated with RNase A before electrophoresis. FIG. 5B is a schematic diagram of the reverse transcription reactions shown in FIG. 5A. The top diagram shows a simple primer extension assay (lane 1) giving rise to a 334 nt cDNA primary product followed by a template jump to generate a ~668 nt product. The bottom diagram shows a reverse transcription reaction that is primed by another RNA molecule. The products of this RNA-primed reaction will be ~334 nt and ~668 nt if the products are treated with RNase A before electrophoresis (lane 2), and ~668 nt and ~1000 nt if not treated with RNase A (lane 3). The self complimentary covalent RNA/cDNA hybrid migrates as a diffuse band at ~600 nt in lane 3, because secondary structures form that affect migration. RNA migrates with a different mobility than single-stranded DNA on these gels. The cDNA products in lane 2 are about 10 nt shorter than those in lane 1 suggesting that RNA-primed cDNA synthesis initiates about 10 nt from the 3' end of the template.

FIG. 6A is an autoradiograph of the reaction products obtained for the RNA-primed reverse transcription and template jumping reactions. All reactions were conducted in the presence of [α-$^{32}$P] dCTP, the absence of DNA primers, and all products were treated with RNase A before electrophoresis. Lane 1, 2.4 pmoles 183 nt vector RNA; lane 2, 2.4 pmoles 254 nt R2 RNA, lane 3, 2.4 pmoles 334 nt vector RNA; lane 4, 2.4 pmoles 183 nt vector RNA+2.4 pmoles 254 nt R2 RNA; and Lane 5, 2.4 pmoles 254 nt R2 RNA+2.4 pmoles 334 nt vector RNA The efficiency of the RNA-priming and of the template jumps were quantified and are presented in Table 2 (see Example 5). FIG. 6B illustrates the junction sequences of template jumps from the 334 nt vector RNA to the 254 nt R2 RNA. An aliquot of the total reaction products shown in lane 5 above was PCR amplified using primers AB.23 (SEQ ID No: 33, Table I) and AB.2b (SEQ ID No: 26, Table I). The PCR products were cloned and random clones sequenced. Shown at the top are the 3' end of the 254 nt RNA template (SEQ ID No: 7) and the 5' end of the 334 nt RNA template (SEQ ID No: 8) used in the reverse transcription reaction. Below these sequences are seven clones derived from the cDNA (SEQ ID Nos: 9–15). Most of the junctions contain additional nucleotides not derived from either of the RNA templates (nucleotides between the dotted vertical lines). Not all cDNA products extended to the end of the 334 nt templates (number of bases deleted are given), but these jumps did not involve short segments of sequence identity with the acceptor RNA.

In FIG. 7B, an image of an autoradiograph illustrates directed template jumps to short 'acceptor' RNA templates. Reverse transcription in each reaction was initiated from a $^{32}$P-end-labeled primer AB.9 (SEQ ID No: 28, Table I) (30 ng) annealed to 30 ng 177 nt 'donor' RNA template. Lane 1 contained 400 ng 334 nt vector RNA, lane 2 contained 400 ng 183 nt vector RNA, and lane 3 contained no acceptor RNA. In FIG. 7A an image of an autoradiograph illustrates directed template jumps to longer 'acceptor' RNA templates. Reverse transcription was again initiated from the $^{32}$P-end-labeled primer AB.9 (SEQ ID No: 28, Table I) (50 ng) annealed to 50 ng 177 nt 'donor' RNA template. Lane 1, 300 ng 334 nt vector RNA; lane 2, 300 ng 600 nt RNA; and lane 3, 300 ng 1090 nt RNA.

In FIG. 8A, all lanes contain 10 ng of $^{32}$P-labeled 254 nt R2 RNA and 10 ng of R2 protein. Lane 1, no other additions; lane 2, 100 ng of the 164 bp target DNA; lane 3, 100 ng of a 50 nt DNA oligonucleotide AB.17 (SEQ ID No: 30, Table 1); lane 4, 100 ng of DdeI digested pBSII(SK–) DNA. In FIG. 8B, lane 1, 20 ng $^{32}$P-labeled target DNA, 15 ng R2 protein, and 100 ng 254 nt R2 RNA; lane 2, 20 ng $^{32}$P-labeled target DNA and 15 ng R2 protein; lane 3, 10 ng OF $^{32}$P-labeled 254 nt R2 RNA, 10 ng of R2 protein and 100 ng of the 164 bp target DNA.

FIG. 11A is a comparison of the structure of the R2 and HIV RTs. The HIV structure is a simplified depiction of the detailed crystallographic studies (Kohlstaedt et al., "Crystal Structure at 3.5 Angstrom Resolution of HIV-1 Reverse Transcriptase Complexed with an Inhibitor," *Science* 256:1783–1790 (1992); Sarafianos et al., "Crystal Structure of HIV-1 Reverse Transcriptase in Complex with a Polypurine Tract RNA:DNA," *EMBO J.* 20:1449–1461 (2001), each of which is hereby incorporated by reference in its entirety). The R2 protein lacks an RNase H domain and has additional segments in the 'fingers and palm' regions of the RT domain. Therefore, unlike the retroviral protein, the R2 protein is depicted as containing most of its affinity for the RNA template upstream of the active site (shaded region). FIG. 11B is a summary of the unusual properties of the R2 protein. Because the 3' end of free RNA can bind downstream of the active site, it can be used to prime reverse transcription. Template jumping is possible because the template binding site upstream of the active site can bind a second RNA before the protein dissociates after reverse transcribing the first RNA template. FIG. 11C illustrates the similarity of RNA-priming and template jumping to models of the integration reaction of R2. RNA-priming can be viewed as similar to the signature step of the TPRT reaction. When the R2 protein is bound to the DNA target site, the 3' end of the cleaved DNA strand can bind downstream of the RT active site. Meanwhile, template jumps may be similar to one mechanism proposed for the attachment of the R2 sequence to the upstream target site after second strand cleavage (Burke et al., "The Domain Structure and Retrotransposition Mechanism of R2 Elements are Conserved Throughout Arthropods," *Mol. Biol. Evol.* 16:502–511 (1999), which is hereby incorporated by reference in its entirety). While there is no direct biochemical evidence for this step, it represents the model that best explains the sequence variation found at the 5' end of endogenous R2 elements (Burke et al., "The Domain Structure and Retrotransposition Mechanism of R2 Elements are Conserved Throughout Arthropods," *Mol. Biol. Evol.* 16:502–511 (1999); and George et al., "Analysis of the 5' Junctions of R2 Insertions with the 28S gene: Implications for non-LTR Retrotransposition," *Genetics* 142:853–863 (1996), each of which is hereby incorporated by reference in its entirety) For both TPRT and 5' attachment, the DNA strands are drawn partially denatured by the R2 protein, as it would seem most similar to what has been shown to occur with RNA.

FIG. 14A is the Phosphoimage scan of lane 3 from FIG. 13. The approximate size of the cDNA products can be calculated relative to 100 nt size standards. FIG. 14B is the similar processivity assay to that conducted in FIG. 13 lane 3 ('trap' reactions), except that the RNA is a 1094 nt vector RNA and the reverse transcription reaction was primed with the end-labeled AB.34 (SEQ ID No: 38, Table I). For each primer extension reaction, 50 fmole of annealed RNA/DNA-primer was used under the same conditions as described for lane 3 in FIG. 13. The products of reverse transcription was separated on 6% denaturing PAGE, scanned using PhosphoImaging function and analyzed using Image Quant.

FIG. 15A is an autoradiograph of different primer extension reactions, which were allowed to proceed for varying lengths of time. End-labeled AB.8 (SEQ ID No: 27, Table I) DNA primer was annealed to an 183 nt RNA template. For each primer extension reaction, about 50 fmole of annealed RNA/DNA-primer was used. The complex dissociation, as a function of time, was assayed by yield of primer extension. For R2 RT reaction, 50 fmole of the template/primer was preincubated with 2 ng (20 fmole) of R2 RT for 15 min at 37° C. under the same conditions as in FIG. 13. After preincubation 2.5 μl of the "trap" (20 μg of heparin, ~1 μg of poly(rA)/poly(dT) 13–18) was added to the preincubation. The addition of the "trap" is considered as a time 0. The mixture was incubated at 37° C. for the lengths of time indicated before the addition of 2.5 μl of 2.5 mM dNTP to start the reaction. All polymerization reactions were conducted for 4 min at 37° C. The products of the reactions were separated on 7% of denaturing polyacrylamide gel and analyzed as described above using PhosphoImager and Image Quant. The fraction of enzyme which remained bound to the template as a function of time was determined based on assumption that the yield of the cDNA accumulation is proportional to the fraction of enzymes that is bind to the template at the moment of addition of dNTP. Reactions with the AMV RT were conducted like that with the R2 RT, except that each reaction contained 2.5 U of AMV RT (Promega) and the preincubation mixture was that recommended for AMV (see FIG. 13). FIG. 15B is a graph comparing the R2 and AMV RT dissociation rates from an RNA template. Open squares, data for R2 RT (average of three experiments); solid circles, data for AMV RT.

FIG. 16A is an autoradiograph illustrating the reaction products of a primed RT reaction. The template in the reaction of FIG. 16A is the 1094 nt RNA, with synthesis primed by end-labeled AB.34 (SEQ ID No: 38, Table I). For each lane, 125 fmole of template/primer was preincubated with 10 ng (100 fmole) of R2 RT for 5 min at 37° C. After preincubation, the reverse transcription was started by addition 5 μl of 1.25 mM dNTP and stopped according to the time in seconds indicated at the top of the Figure by quick mixing with 3 volume of ethanol containing 0.3M sodium acetate (pH 5.2) and 1% SDS. After precipitation, the products were separated on 6% denaturing PAGE and analyzed using PhosphorImager and Image Quant. FIG. 16B illustrates a similar elongation assay using the 600 nt RNA primed with AB.23 (SEQ ID No: 33, Table I) and either the R2 and AMV RT. Plotted in this Figure is the longest polymerization products detected on denaturing polyacrylamide gels like that in FIG. 16A. The maximal rate of elongation was determined by a fitting of the data points with a linear function. Circles, the R2 data points; triangles, the AMV data points.

DETAILED DESCRIPTION OF THE INVENTION

Figure 2:
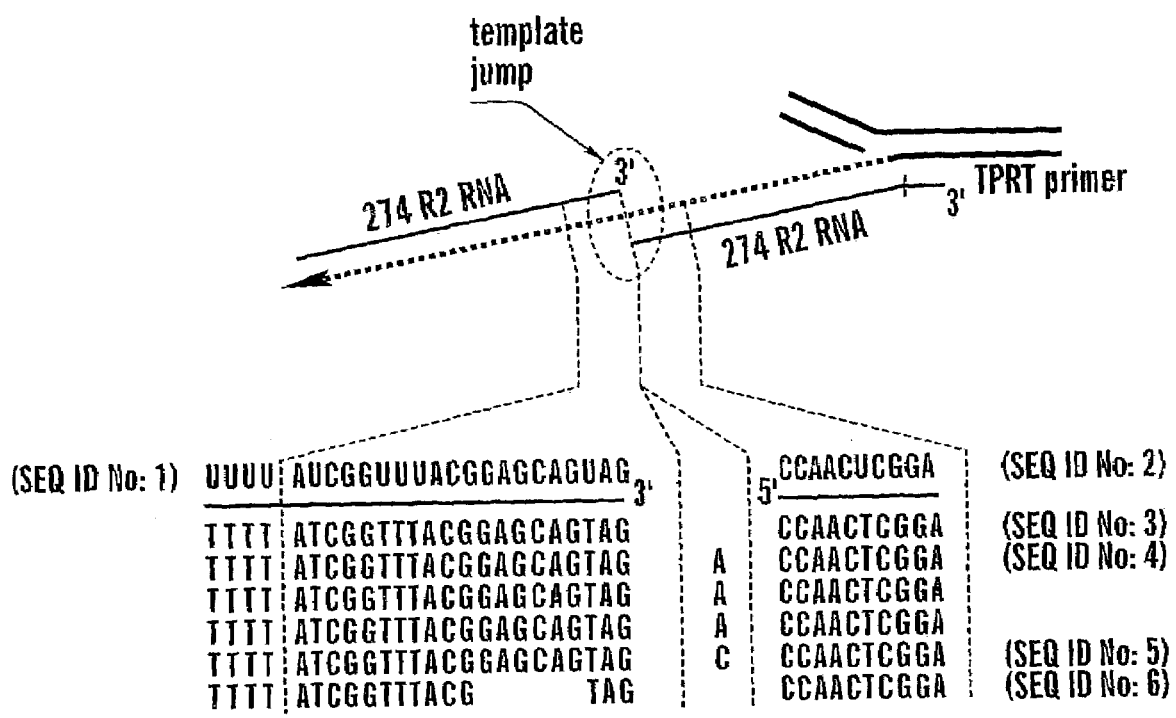
FIG. 2 illustrates the various junction sequences resulting from the template jumps in FIG. 1B. The presumed mechanism for the generation of the ~638 nt TPRT product in FIG. 1B is diagramed at the top of this figure. Reverse transcription is initiated 20 nt from the 3' end of the RNA at the beginning of R2 3' UTR. When the RT reaches the 5' end of the first template (donor) it jumps to the free 3' end of a second RNA template. To obtain the cDNA sequence corresponding to these jumps, the ~638 nt TPRT product from FIG. 1B, lane 2, was purified from the gel and the junction region amplified by PCR using primers AB.18 (SEQ ID No: 31, Table I) and AB.19 (SEQ ID No: 32, Table I). At the bottom of the Figure are the junctions derived from six cloned PCR products. The top sequence represents the 5' and 3' ends of 274 nt R2 RNA. Four of the junctions contain an extra nucleotide (nucleotides between the inner dotted vertical lines) while one junction contains a 6 nt internal deletion of the acceptor RNA. SEQ ID Nos: 1 and 2 are, respectively, the 3'-terminal and 5'-terminal sequences of the 274 base R2 RNA. SEQ ID Nos: 3–6 are the nucleotide sequences of the junction region of cDNA RT products.

Preferred non-LTR retrotransposon proteins or polypeptides are the proteins or polypeptides of R2 elements.

One preferred protein possessing reverse transcriptase activity and encoded by a non-LTR retrotransposable R2 element is the protein encoded by the R2 element of *Bombyx mori*. This protein has an amino acid sequence corresponding to SEQ ID No: 22 as follows:

```
Met Met Ala Ser Thr Ala Leu Ser Leu Met Gly Arg Cys Asn Pro Asp
                 5                  10                  15

Gly Cys Thr Arg Gly Lys His Val Thr Ala Ala Pro Met Asp Gly Pro
             20                  25                  30

Arg Gly Pro Ser Ser Leu Ala Gly Thr Phe Gly Trp Gly Leu Ala Ile
             35                  40                  45

Pro Ala Gly Glu Pro Cys Gly Arg Val Cys Ser Pro Ala Thr Val Gly
         50                  55                  60

Phe Phe Pro Val Ala Lys Lys Ser Asn Lys Glu Asn Arg Pro Glu Ala
     65                  70                  75                  80

Ser Gly Leu Pro Leu Glu Ser Glu Arg Thr Gly Asp Asn Pro Thr Val
                 85                  90                  95

Arg Gly Ser Ala Gly Ala Asp Pro Val Gly Gln Asp Ala Pro Gly Trp
             100                 105                 110
```

-continued

Thr Cys Gln Phe Cys Glu Arg Thr Phe Ser Thr Asn Arg Gly Leu Gly
         115                 120                 125

Val His Lys Arg Arg Ala His Pro Val Glu Thr Asn Thr Asp Ala Ala
    130                 135                 140

Pro Met Met Val Lys Arg Trp His Gly Glu Glu Ile Asp Leu Leu
145                 150                 155                 160

Ala Arg Thr Glu Ala Arg Leu Leu Ala Glu Arg Gly Gln Cys Ser Gly
             165                 170                 175

Gly Asp Leu Phe Gly Ala Leu Pro Gly Phe Gly Arg Thr Leu Glu Ala
             180                 185                 190

Ile Lys Gly Gln Arg Arg Glu Pro Tyr Arg Ala Leu Val Gln Ala
         195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Gln Gln Arg Cys Ala Glu Asp Ala Ala Tyr Asp Pro Ser Ala Val
             245                 250                 255

Gly Gln Met Ser Pro Asp Ala Ala Arg Val Leu Ser Glu Leu Leu Glu
         260                 265                 270

Gly Ala Gly Arg Arg Arg Ala Cys Arg Ala Met Arg Pro Lys Thr Ala
             275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
             325                 330                 335

Cys Gly Gly Val Gly His Ser Leu Glu Glu Met Glu Thr Tyr Trp Arg
             340                 345                 350

Pro Ile Leu Glu Arg Val Ser Asp Ala Pro Gly Pro Thr Pro Glu Ala
         355                 360                 365

Leu His Ala Leu Gly Arg Ala Glu Trp His Gly Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
             405                 410                 415

Trp Arg Ala Val Pro Val His Leu Lys Ala Glu Met Phe Asn Ala Trp
             420                 425                 430

Met Ala Arg Gly Glu Ile Pro Glu Ile Leu Arg Gln Cys Arg Thr Val
         435                 440                 445

Phe Val Pro Lys Val Glu Arg Pro Gly Gly Pro Gly Glu Tyr Arg Pro
    450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
             485                 490                 495

Ile Cys Ala Asp Gly Thr Leu Glu Asn Ser Ala Val Leu Asp Ala Val
         500                 505                 510

Leu Gly Asp Ser Arg Lys Lys Leu Arg Glu Cys His Val Ala Val Leu
    515                 520                 525

-continued

Asp Phe Ala Lys Ala Phe Asp Thr Val Ser His Glu Ala Leu Val Glu
530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
            565                 570                 575

Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
            595                 600                 605

Pro Glu Arg Val Gly Tyr Arg Leu Glu Met Glu Leu Val Ser Ala Leu
            610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
            675                 680                 685

Gly Lys Pro Leu Arg Gln Val Ser Cys Val Glu Arg Trp Arg Tyr Leu
690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
            755                 760                 765

Gln Ile Arg Lys Ala Val Gly Gln Trp Leu Arg Leu Pro Ala Asp Val
            770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
            805                 810                 815

Gly Leu Asp Ser Ser Pro Trp Ser Val Ala Arg Ala Ala Lys Ser
            820                 825                 830

Asp Lys Ile Arg Lys Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
            915                 920                 925

Glu Ser Ser Leu Thr Cys Arg Ala Gly Cys Lys Val Arg Glu Thr Thr
930                 935                 940

-continued

```
Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
            965                 970                 975

Lys Trp Thr Val Glu Leu Glu Pro Arg Leu Arg Thr Ser Val Gly Leu
        980                 985                 990

Arg Lys Pro Asp Ile Ile Ala Ser Arg Asp Gly Val Gly Ile Val
    995                 1000                1005

Asp Val Gln Val Val Ser Gly Gln Arg Ser Leu Asp Glu Leu His Arg
    1010                1015                1020

Glu Lys Arg Asn Lys Tyr Gly Asn His Gly Glu Leu Val Glu Leu Val
1025                1030                1035                1040

Ala Gly Arg Leu Gly Leu Pro Lys Ala Glu Cys Val Arg Ala Thr Ser
                1045                1050                1055

Cys Thr Ile Ser Trp Arg Gly Val Trp Ser Leu Thr Ser Tyr Lys Glu
            1060                1065                1070

Leu Arg Ser Ile Ile Gly Leu Arg Glu Pro Thr Leu Gln Ile Val Pro
        1075                1080                1085

Ile Leu Ala Leu Arg Gly Ser His Met Asn Trp Thr Arg Phe Asn Gln
    1090                1095                1100

Met Thr Ser Val Met Gly Gly Gly Val Gly
1105                1110
```

This protein is further characterized as also possessing endonuclease activity. It is encoded by a DNA molecule having a nucleotide sequence corresponding to SEQ ID No: 23 as follows.

```
atgatggcga gcaccgcact gtcccttatg ggacggtgta acccggatgg ctgtacacgt    60
ggtaaacacg tgacagcagc ccgatggac ggaccgcgag gaccgtcaag cctagcaggt   120
accttcgggt ggggccttgc gatacctgcg ggcgaaccct gtggtcgggt ttgcagcccg   180
gccacagtgg gttttttttcc tgttgcaaaa aagtcaaata aagaaaatag acctgaagcc   240
tctggcctcc cgctggagtc agagaggaca ggcgataacc cgactgtgcg gggttccgcc   300
ggcgcagatc ctgtgggtca ggatgcgcct ggttggacct gccagttctg cgaacgaacc   360
ttttcgacca acaggggttt gggtgtccac aagcgtagag cccacctgt tgagaccaat   420
acggatgccg ctccgatgat ggtgaagcgg cggtggcatg gcgaggaaat cgacctcctc   480
gctcgcaccg aggccaggtt gctcgctgag cgggtcagt gctcgggtgg agacctcttt   540
ggcgcgcttc caggtttgg aagaactctg gaagcgatta aggacaacg gcggagggag   600
ccttatcggg cattggtgca agcgcacctt gcccgatttg gttcccagcc gggtccctcg   660
tcgggggggt gctcggccga gcctgacttc cggcgggctt ctggagctga ggaagcgggc   720
gaggaacgat gcgccgaaga cgccgctgcc tatgatccat ccgcagtcgg tcagatgtcg   780
cccgatgccg ctcgggttct ctccgaactc cttgagggtg cggggagaag acgagcgtgc   840
agggctatga gacccaagac tgcagggcgg cgaaacgatt tgcacgatga tcggacagct   900
agtgcccaca aaaccagtag acaaaagcgc agggcagagt acgcgcgtgt gcaggaactg   960
tacaagaagt gtcgcagcag agcagcagct gaggtgatcg atggcgcgtg tgggggtgtc  1020
ggacactcgc tcgaggagat ggagacctat ggcgaccta tcctcgagag agtgtccgat  1080
gcacctggc ctacaccgga agctcttcac gccctaggc gtgcggagtg cacgggggc  1140
aatcgcgact acacccagct gtggaagccg atctcggtgg aagagatcaa ggcctcccgc  1200
```

-continued

```
tttgactggc gaacttcgcc gggcccggac ggtatacgtt cgggtcagtg gcgtgcggtt 1260
cctgtgcact tgaaggcgga aatgttcaat gcatggatgg cacgaggcga aatacccgaa 1320
attctacggc agtgccgaac cgtctttgta cctaaggtgg agagaccagg tggaccgggg 1380
gaatatcgac cgatctcgat cgcgtcgatt cccctgagac actttcactc catcttggcc 1440
cggaggctgt tggcttgctg cccccctgat gcacgacagc gcggatttat ctgcgccgac 1500
ggtacgctgg agaattccgc agtactggac gcggtgcttg gggatagcag gaagaagctg 1560
cgggaatgtc acgtggcggt gctagacttc gccaaggcat ttgacacagt gtctcacgag 1620
gcacttgtcg aattgctgag gttgaggggc atgcccgaac agttctgcgg ctacattgct 1680
cacctatacg atacggcgtc caccaccttc gccgtgaaca atgaaatgag cagccctgta 1740
aaagtgggac gaggggttcg tcaaggggac cctctgtcgc cgatactctt caacgtggtg 1800
atggacctca tcctggcttc cctgccggag agggtcgggt ataggttgga gatggaactc 1860
gtgtccgctc tggcctatgc tgacgaccta gtcctgcttg cggggtcgaa ggtagggatg 1920
caggagtcca tctctgctgt ggactgtgtc ggtaggcaga tgggcctacg cctgaattgc 1980
aggaaaagcg cggttctgtc tatgataccg gatggccacc gcaagaagca tcactacctg 2040
actgagcgaa ccttcaatat tggaggtaag ccgctcaggc aggtgagttg tgttgagcgg 2100
tggcgatatc ttggtgtcga ttttgaggcc tctggatgcg tgacattaga gcatagtatc 2160
agtagtgctc tgaataacat ctcaagggca cctctcaaac cccaacagag gttggagatt 2220
ttgagagctc atctgattcc gagattccag cacggttttg tgcttggaaa catctcggat 2280
gaccgattga gaatgctcga tgtccaaatc cggaaagcag tcggacagtg gctaaggcta 2340
ccggcggatg tgcccaaggc atattatcac gccgcagttc aggacggcgg cttagcgatc 2400
ccatcggtgc gagcgaccat cccggacctc attgtgaggc gtttcggggg gctcgactcg 2460
tcaccatggt cagtggcaag agccgccgcc aaatctgata agattcgtaa gaaactgcgg 2520
tgggcctgga acagctccg caggttcagc cgtgttgact ccacaacgca acgaccatct 2580
gtgcgcttgt tttggcgaga acatctgcat gcatctgttg atggacgcga acttcgcgaa 2640
tccacacgca ccccgacatc cacaaagtgg attagggagc gatgcgcgca gataaccgga 2700
cgggacttcg tgcagttcgt gcacactcat atcaacgccc tcccatcccg cattcgcgga 2760
tcgagagggc gtagaggtgg gggtgagtct tcgttgacct gccgtgctgg ttgcaaggtt 2820
agggagacga cggctcacat cctacaacag tgtcacagaa cacacggcgg ccggattcta 2880
cgacacaaca agattgtatc tttcgtggcg aaagccatgg aagagaacaa gtggacggtt 2940
gagctggagc cgaggctacg aacatcggtt ggtctccgta agccggatat tatcgcctcc 3000
agggatggtg tcggagtgat cgtggacgtg caggtggtct cgggccagcg atcgcttgac 3060
gagctccacc gtgagaaacg taataaatac gggaatcacg gggagctggt tgagttggtc 3120
gcaggtagac taggacttcc gaaagctgag tgcgtgcgag ccacttcgtg cacgatatct 3180
tggaggggag tatggagcct gacttcttat aaggagttaa ggtccataat cgggcttcgg 3240
gaaccgacac tacaaatcgt tccgatactg gcgttgagag gttcacacat gaactggacc 3300
aggttcaatc agatgacgtc cgtcatgggg ggcggcgttg gttga                 3345
```

The complete amino acid and cDNA nucleotide sequences are also reported, respectively, at Genbank Accession Nos. AAB59214 and M16558, each of which is hereby incorporated by reference in its entirety.

In addition to the protein encoded by the R2 element of *Bombyx mori*, other proteins possessing reverse transcriptase activity which are encoded by different non-LTR retrotransposable R2 elements can also be employed in the methods of the present invention. A number of other arthropods are known to harbor R2 elements which exhibit a similar structure to the R2 element of Bombyx mori (Burke et al., "The Domain Structure and Retrotransposition Mechanism of R2 Elements Are Conserved Throughout Arthropods," *Mol. Biol. Evol.* 16(4):502–511 (1999); Yang et al., "Identification of the Endonuclease Domain Encoded by R2 and Other Site-Specific, Non-Long Terminal Repeat Retrotransposable Elements," *Proc. Natl. Acad. Sci. USA* 96:7847–7852 (1999), each of which is hereby incorporated by reference in its entirety). The R2 elements of other arthropods include, without limitation, R2 elements from *Drosophila* spp. (fruit fly), *Forficula auricularia* (earwig), *Popillia japonica* (Japanese beetle), *Nasonia vitripennis* (jewel wasp), *Tenebrio molitor* (mealworm), *Collembola* spp. (springtails), *Isopoda* spp. (pillbugs), and *Limulus polyphemus* (horseshoe crab).

The protein and encoding DNA sequences for the R2 element of *D. melanogaster* are reported, respectively, at Genbank Accession Nos. P16423 and X51967, each of which is hereby incorporated by reference in its entirety. The protein and encoding DNA sequences for the R2 element of *D. mercatorum* are reported, respectively, at Genbank Accession Nos. AAB94032 and AF015685, each of which is hereby incorporated by reference in its entirety. The protein and encoding DNA sequences for the R2 element of *P. japonica* are reported, respectively, at Genbank Accession Nos. AAB66358 and L00949, each of which is hereby incorporated by reference in its entirety. The protein and encoding DNA sequences for the R2 element of *N. vitripennis* are reported, respectively, at Genbank Accession Nos. AAC34927 and L00950, each of which is hereby incorporated by reference in its entirety.

Other non-LTR retrotransposon elements and their proteins can be readily identified by isolating putative non-LTR retrotransposon element proteins and testing them for homology with the above-listed R2 proteins as well as testing them for endonuclease and target-primed reverse transcriptase activity as described, for example, in Luan et al., "Reverse Transcription of R2Bm RNA is Primed by a Nick at the Chromosomal Target Site: A Mechanism for Non-LTR Retrotransposition," *Cell* 72:595–605 (1993); Luan et al., "RNA Template Requirements for Target DNA-Primed Reverse Transcription by the R2 Retrotransposable Element," *Mol. Cell Biol.* 15(7):3882–3891 (1995); Luan et al., "Downstream 28S Gene Sequences on the RNA Template Affect the Choice of Primer and the Accuracy of Initiation by the R2 Reverse Transcriptase," *Mol. Cell Biol.* 16(9):4726–4734 (1996), each of which is hereby incorporated by reference in its entirety. Once identified, DNA molecules encoding the non-LTR retrotransposon protein can be isolated using standard techniques known to those skilled in the art.

Fragments of the above-identified non-LTR retrotransposon proteins can also be utilized in accordance with the present invention. It has previously been demonstrated that the protein encoded by the R2 element of a number of arthropods possess multiple functional domains, including an N-terminal DNA binding domain, a central reverse transcriptase domain, and a C-terminal endonuclease domain (Burke et al., "The Domain Structure and Retrotransposition Mechanism of R2 Elements Are Conserved Throughout Arthropods," *Mol. Biol. Evol.* 16(4):502–511 (1999); Yang et al., "Identification of the Endonuclease Domain Encoded by R2 and Other Site-Specific, Non-Long Terminal Repeat Retrotransposable Elements," *Proc. Natl. Acad. Sci. USA* 96:7847–7852 (1999), each of which is hereby incorporated by reference in its entirety).

Suitable fragments can be produced by several means. Subclones of the gene encoding a known non-LTR retrotransposon protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for reverse transcriptase activity, e.g., using known procedures or procedures set forth in U.S. Pat. No. 6,100,039 to Burke et al. and U.S. Pat. No. 6,132,995 to Gronowitz et al., each of which is hereby incorporated by reference in its entirety.

In another approach, based on knowledge of the primary structure of the non-LTR retrotransposon protein, fragments of the gene may be synthesized using the PCR technique together with specific sets of primers chosen to represent particular portions of the protein, i.e., encoding a fragment having reverse transcriptase activity (see Erlich et al., "Recent Advances in the Polymerase Chain Reaction," *Science* 252:1643–51 (1991), which is hereby incorporated by reference in its entirety). These can then be cloned into an appropriate vector for expression of a truncated protein or polypeptide from bacterial cells.

Fusion proteins which include the reverse transcriptase can also be used in accordance with the invention. Such fusion proteins may comprise, for example, a carrier protein which has a leader sequence of hydrophobic amino acids at the amino terminus of the reverse transcriptase domain. This carrier protein is normally excreted through the membrane of the cell within which it is made. By cleavage of the hydrophobic leader sequence during excretion, a means is provided for producing a polypeptide having reverse transcriptase activity, which can be recovered either from the periplasmic space or the medium in which the bacterium is grown. The use of such a carrier protein allows isolation of polypeptides having reverse transcriptase activity without contamination by other proteins within the bacterium, and may achieve production of a form of reverse transcriptase having greater stability by avoiding the enzymes within the bacterial cell which degrade foreign proteins. The DNA and amino acid sequences for such hydrophobic leader sequences, as well as methods of preparing such fusion proteins are taught, e.g., in U.S. Pat. No. 4,411,994 to Gilbert et al., which is hereby incorporated by reference in its entirety.

It is also possible to prepare fusion proteins comprising a polypeptide having reverse transcriptase activity that is linked via peptide bond at the amino or carboxy termini with polypeptides which stabilize or change the solubility of the polypeptide having reverse transcriptase activity. An amino-terminal gene fusion which encodes reverse transcriptase, having both DNA polymerase and RNase activity, and trpE is taught, e.g., by Tanese et al., *Proc. Natl. Acad. Sci. USA* 82:4944–4948 (1985), which is hereby incorporated by reference in its entirety. A carboxy-terminal gene fusion which encodes reverse transcriptase and part of the plasmid pBR322 tet gene is taught, e.g., by Kotewicz et al., *Gene*

35:249–258 (1985); and Gerard, *DNA* 5:271–279 (1986), each of which is hereby incorporated by reference in its entirety.

A DNA molecule encoding the non-LTR retrotransposon protein or polypeptide having reverse transcriptase activity can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. Depending on the vector, the DNA molecule can be ligated to appropriate regulatory sequences either prior to its insertion into the vector (i.e., as a chimeric gene) or at the time of its insertion (i.e., thereby forming the chimeric gene). The DNA molecule can be cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/– or KS+/– (see "Stratagene Cloning Systems" Catalog (1993) from Stratagene, La Jolla, Calif., which is hereby incorporated by reference in its entirety), pQE, pIHS21, pGEX, pET series (see Studier et. al., "Use of T7 RNA Polymerase to Direct Expression of Cloned Genes," *Gene Expression Technology*, vol. 185 (1990), which is hereby incorporated by reference in its entirety), and any derivatives thereof. Suitable vectors are continually being developed and identified.

Recombinant molecules can be introduced into host cells via transformation, transduction, conjugation, mobilization, or electroporation.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters typically are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as tip, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the DNA molecules encoding the non-LTR retrotransposon protein or polypeptide having reverse transcriptase activity, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The transformed hosts of the inventions may be cultured under protein producing conditions according to any of the methods which are known to those skilled in the art.

The non-LTR retrotransposon protein or polypeptide having reverse transcriptase activity may be isolated according to conventional methods known to those skilled in the art. For example, the cells may be collected by centrifugation, washed with suitable buffers, lysed and sonicated, and the reverse transcriptase isolated by column chromatography, for example, on DEAE-cellulose, phosphocellulose (see Kotewicz et al., *Gene* 35:249–258 (1985), which is hereby incorporated by reference in its entirety) or other standard isolation and identification techniques using, for example, polyribocytidylic acid-agarose, or hydroxylapatite or by electrophoresis or immunoprecipitation. The non-LTR retrotransposon protein or polypeptide is preferably produced in purified form (preferably, at least about 80%, more preferably at least about 90%, pure).

Having expressed and isolated the non-LTR retrotransposon protein or polypeptide, it can subsequently be used in accordance with the present invention.

According to one aspect of the present invention the non-LTR retrotransposon protein or polypeptide is used to prepare cDNA from RNA. This can be achieved by contacting an RNA molecule, in the presence of dNTPs, with a non-LTR retrotransposon protein or polypeptide having reverse transcriptase activity (as described above) under conditions effective for production of a cDNA molecule complementary to the RNA molecule, where the contacting is carried out in the absence of a target DNA molecule of the non-LTR retrotransposon protein or polypeptide. Thereafter, the resulting cDNA can be isolated.

Figure 12:
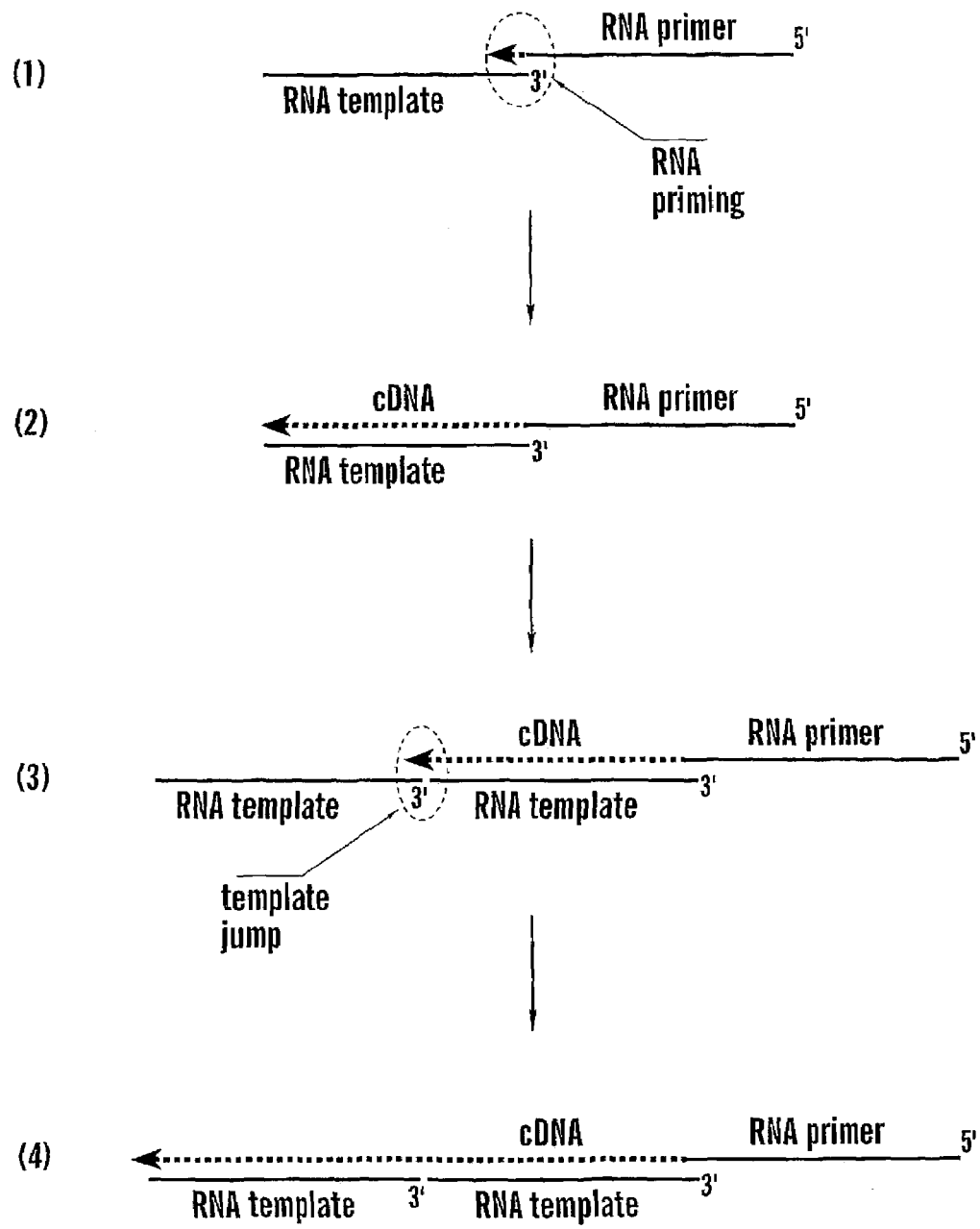
FIG. 12 is a diagram which illustrates a method of preparing cDNA according to the present invention, which may include RNA-priming and template jumping steps. Gray lines represent RNA templates; and dotted lines represent cDNA product. The initial components of the reaction are RNA (either template RNA, donor RNA, or acceptor RNA), the non-LTR retrotransposon RT, and dNTPs. The R2 RT can use the 3' end of one RNA molecule to prime reverse transcription of a second RNA molecule (RNA priming). The two RNA molecules can be the same or different. After reverse transcription to the end of the second RNA, R2 RT can jump to a third RNA molecule (again, the same or different) and continue reverse transcription (template jumping). Both RNA-priming and template jumping do not require sequence identity between the RNAs involved.

Basically, in the presence of RNA (i.e., a plurality of RNA molecules) and dNTPs, the non-LTR retrotransposon protein or polypeptide will use the 3' end of one RNA molecule to prime reverse transcription of another RNA, which can be the same or different from the RNA acting as primer. This is illustrated in step (1) of FIG. 12. The protein or polypeptide, characterized by a high degree of processivity, will likely continue to the end of the RNA template as shown in step (2), at which point it may, but need not, jump to a second RNA template as shown in step (3). Reverse transcription is again likely to continue to the end of the second RNA template as shown in step (4). Another template jump may or may not occur. In most instances, one or more of the RNA molecules which are reverse transcribed will include a region of interest (i.e., for which one or more cDNA copies are desired). It may also be desired to specifically include in the reaction mixture acceptor and/or donor RNA molecules having known sequences. Their known sequences can be used to anneal primers for subsequent amplification procedures (infra).

The target DNA sequences for a number of different non-LTR retrotransposons, in particular R2 elements, have been identified previously (Burke et al., "The Domain Structure and Retrotransposition Mechanism of R2 Elements Are Conserved Throughout Arthropods," *Mol. Biol. Evol.* 16(4):502–511 (1999), which is hereby incorporated by reference in its entirety). For the R2 element of *Bombyx mori*, the target DNA molecule has a nucleotide sequence according to SEQ ID No: 24 as follows:

taaacggcgg gagtaactat gactctctta aggtagccaa atgcctcgtc 50

The cleavage site is between positions 31 and 32 of SEQ ID No: 24. The nick site on the opposite strand is two bases downstream from the cleavage site (Luan et al., "Reverse Transcription of R2Bm RNA Is Primed by a Nick at the Chromosomal Target Site: A Mechanism for non-LTR Retrotransposition," *Cell* 72:595–605 (1993), which is hereby incorporated by reference in its entirety).

There is preferably a sufficient time delay between the steps of contacting and isolating, as described above. Suitable time delays include, without limitation, preferably at least about 30 seconds, more preferably between about 1 minute and 2 hours minutes, even more preferably between about 10 minutes and 2 hours. The synthesis of a complete cDNA may be accomplished by adding the R2 protein or polypeptide and all four dNTPs with the RNA template. The reverse transcription can be carried out under substantially isothermic conditions or under variable temperature conditions. Suitable temperatures range from about 20° C. to about 40° C., preferably about 21° C. to about 35° C., and most preferably at about 22° C. to about 32° C. The particular temperature employed will depend, at least in part on the desired cDNA product one wishes to obtain, as a greater percentage of full length cDNA products can be obtained using temperatures at about 25° C. (i.e., about 22° C. to about 28° C.), while an increase in the total yield of cDNA product can be achieved at higher temperatures.

Use of the non-LTR retrotransposon protein or polypeptide, in particular the R2 protein or polypeptide, offers a number of distinct advantages over retroviral reverse transcriptases. With respect to the RNA molecule, the RNA does not need a particular primer site; hence, it does not require a polyadenylation region as needed by retroviral RT. However, when polyadenylated RNA molecules are reverse transcribed, the polyadenylated region affords a primer binding site that can be used for primer-directed cDNA extension, resulting in a known polyT region at the 5' end of a cDNA molecule. In addition, non-LTR retrotransposon proteins or polypeptides like the R2 protein or polypeptide are capable of carrying out reverse transcription irrespective of the RNA structure. Retroviral RTs frequently stop at certain sequences or in regions which contain a secondary structure, such as stem or stem/loop formations or duplex formations upstream of the template extension, whereas the R2 protein or polypeptide does not.

With respect to the reverse transcription process, the R2 protein or polypeptide is characterized by a significantly greater processivity than retroviral reverse transcriptases. The R2 protein or polypeptide is characterized by a speed of about 880 nt per minute, which is comparable to retroviral reverse transcriptases. More important, though, is the stability of the R2 protein or polypeptide once it has started reverse transcription. Because of its stability, the R2 protein or polypeptide is capable of preparing a population of cDNAs where a significant portion of the cDNA molecules are substantially full length reverse transcripts of the RNA template. By substantially full length, it is intended that the cDNAs are at least about 85 percent of the RNA template length, more preferably at least about 90 percent of the RNA template length, even more preferably about 95 percent of the RNA template length. By significant portion, it is intended to denote at least twice as much as can be prepared using the AMV reverse transcriptase. For example, using a 600 nt template at about 25° C., the R2 protein or polypeptide can prepare a population of cDNA molecules where about 22% are full length while the AMV RT, using the same template at about 37° C. can only prepare a population of cDNA molecule where about 1.2% are full length.

According to another aspect of the present invention, the initial reverse transcription process is followed by amplification procedure, whereby the isolated cDNA is amplified using any one of a number of suitable amplification procedures.

By way of example, the PCR amplification can be performed following isolation of the cDNA. Because the PCR utilizes primers to initiate second strand synthesis, the cDNA molecules prepared during the reverse transcription process should be labeled at their 5' ends with a sequence which will hybridize with suitable PCR primers. Two approaches can be utilized to label the cDNAs.

According to one approach, an oligoC tail can be added at the 3' end of the cDNA transcripts by incubating them with terminal transferase and dCTPs (Chang et al., Nature 275:617–624 (1978); Maniatis et al., Molecular Cloning, Cold Spring Harbor Laboratory (1982), each of which is hereby incorporated by reference in its entirety). A primer which anneals to the oligoC tail can be used in subsequent PCR amplification.

According to a second approach, where the sequence of only a portion of an RNA molecule is known, directed template jumping can be employed to prepare cDNAs starting within the known sequence of the RNA, extending through the unknown sequence (i.e., region of interest) at its 5' end and having a known sequence located at the 5' end. This cDNA is immediately available for PCR amplification, because the unknown sequence (i.e., region of interest) is flanked by known sequences which can be annealed by PCR primers. Alternatively, the 3' end of a partially known RNA molecule can be obtained again using the template jumping ability of R2. Reverse transcription is primed from a known donor RNA sequence, the reverse transcriptase jumps to the 3' end of the partially known RNA and continues synthesis past the region of known sequence. PCR amplification is again possible, because the cDNA product contains its unknown sequences (i.e., region of interest) flanked by known sequences which can be annealed by primers.

Basically, the PCR process is carried out in step-wise fashion using alternating steps of annealing primers, extending primers to achieve complementary strand synthesis, followed by strand dissociation. Beginning with an isolated ss cDNA (or pool of ss cDNAs) containing a region of interest, a first primer is annealed to the ss cDNA molecule at a position 3' of the region of interest and then the primer is extended to form a complementary DNA strand including a complement of the region of interest. This complementary DNA strand can then be dissociated from the ss cDNA, at which time it is available for annealing by a second primer at a position 3' of the complement of the region of interest. Primer extension is carried out to form a second complementary DNA strand which is substantially the same as the single-stranded cDNA molecule at the region of interest. Upon dissociating the second complementary cDNA molecule from the complementary DNA strand, the entire process can be repeated indefinitely to amplify the quantity of cDNA which contain the region of interest or a complement thereof.

The non-LTR retrotransposon protein or polypeptide is ideally suited for incorporation into a kit which is useful for the preparation of cDNA from RNA. Such a kit may include a carrier device compartmentalized to receive one or more containers, such as vials, tubes, and the like, each of which includes one of the separate elements used to prepare cDNA from RNA. For example, there may be provided a first container, the contents of which include the non-LTR protein or polypeptide in solution. Further, any number of additional containers can be provided, the contents of which independently include suitable buffers, substrates for DNA synthesis such as the deoxynucleotide triphosphates (e.g., dATP, dCTP, dGTP, and dTTP) either individually or collectively in a suitable solution, a terminal transferase in solution, donor RNA having a known nucleotide sequence for use as an RT primer to obtain a 3' end of RNA, and acceptor RNA having a known nucleotide sequence to obtain a 5' end of RNA. Any combinations of the above components can be provided.

The R2 protein or polypeptide may be present at about 0.1 μg/ml to about 1 μg/ml, preferably about 200 ng/ml to about 500 ng/ml. The buffer conditions for the reverse transcription can range from about 50 to about 200 mM NaCl, about 1–10 mM $MgCl_2$, about 0.0 to 0.2% Triton X-100, about 10 to about 250 μM triphosphates, at a pH from about 7 to about 8.5. The donor and acceptor RNAs for template jumps can be at concentration from about 0.5 to about 20 μg/ml. The terminal transferase, if employed, may be present at a concentration of about 0.1 μg/ml to about 100 μg/ml, preferably about 5 μg/ml to about 50 μg/ml.

EXAMPLES

The following examples are provided to illustrate embodiments of the present invention, but they are by no means intended to limit its scope. The materials and methods described below were utilized in the following examples.

Preparations of Target DNA

The DNA substrate for the TPRT reaction was a 164 nt segment of the 28S rRNA gene generated by PCR amplification from clone pB109 using primer AB.j44 (SEQ ID No: 37, Table I) complementary to the 28S sequence 54 bp upstream of the R2 insertion site and primer AB.25 complementary to the region 110 bp downstream of the R2 site. The PCR was carried out in 50 μl reactions containing 10 ng of pB109, 200 ng each primer, 50 μCi of [α-$^{32}$P] dCTP (3,000 Ci/mmol, New England Nuclear), 200 μM each dATP, dGTP and dTTP, and 100 μM dCTP, 2.5–5 U Taq DNA polymerase (Life Technologies). The length of the DNA strand designed to be used as primer was twice as long as that used in previous assays (Yang and Eickbush, "RNA-induced Changes in the Activity of the Endonuclease Encoded by the R2 Retrotransposable Element," Mol. Cell. Biol 18:3455–3465 (1998); Yang et al., "Identification of the Endonuclease Domain Encoded by R2 and Other Site-specific, non-Long Terminal Repeat Retrotransposable Elements," Proc. Natl. Acad. Sci. USA 96:7847–7852 (1999), each of which is hereby incorporated by reference in its entirety) in order to increase the number of α-$P^{32}$ CTPs that could be incorporated by PCR and, thus, increase the sensitivity of the assay. The PCR amplification products were separated on 8% native polyacrylamide gels, the 164 bp band was cut from the gel, and eluted at room temperature in 0.3M sodium acetate pH 5.2, 0.03% SDS. The elution buffer was extracted with phenol/chloroform and the DNA recovered by ethanol precipitation.

Preparations of RNA Templates

All RNA templates were generated by in vitro run-off transcription using either T7 or T3 RNA polymerase (Fermentas Inc., Life Technologies). Templates were either restriction digested pBSII(SK−) plasmids or PCR amplified products containing the T7 promoter. The 254 nt R2 RNA was transcribed from a template generated by PCR amplification of pBmR2-249A4 (Luan et al., "Reverse Transcription of R2Bm RNA is Primed by a Nick at the Chromosomal Target Site: A Mechanism for non-LTR Retrotransposition," *Cell* 72:595–605 (1993), which is hereby incorporated by reference in its entirety) using primers AB.13 (SEQ ID No: 29, Table I) and AB.2b (SEQ ID No: 26, Table I). The 274 nt R2 RNA was transcribed from a template generated by PCR amplification of R2Bm249V5'3' (Luan and Eickbush, "Downstream 28S Gene Sequences on the RNA Template Affect the Choice of Primer and the Accuracy of Initiation by the R2 Reverse Transcriptase," *Mol. Cell. Biol.* 16:4726–4734 (1996), which is hereby incorporated by reference in its entirety) using primers AB.13 (SEQ ID No: 29, Table I) and AB.9 (SEQ ID No: 28, Table I). These R2 RNA templates differed from those used previously ((Yang and Eickbush, "RNA-induced Changes in the Activity of the Endonuclease Encoded by the R2 Retrotransposable Element," *Mol. Cell. Biol.* 18:3455–3465 (1998); Yang et al, "Identification of the Endonuclease Domain Encoded by R2 and Other Site-specific, non-Long Terminal Repeat Retrotransposable Elements," *Proc. Natl. Acad. Sci. USA* 96:7847–7852 (1999), each of which is hereby incorporated by reference in its entirety), in that the RNA did not included 30 nt of pBSII(SK−) sequence at the 5' end of the RNA. The presence of these C-rich plasmid sequences reduce the efficiency of the TPRT reaction.

Endonuclease Encoded by the Retrotransposon R2Bm," *Cell* 55:235–246 (1988), which is hereby incorporated by reference in its entirety).

The in vitro transcription was performed in 80 µl volumes containing 2–5 µg of pre-digested plasmid DNA or gel purified PCR fragments, 16 µl 5×transcription buffer, 1 mM each NTP and 150 U of T7 or T3 RNA polymerase (Fermentas Inc., Life Technologies). Reactions were incubated at 37° C. until a pyrophosphate precipitation formed (approximately 1.5 hr). After synthesis the samples were diluted 2-fold, mixed with DNase I buffer and the DNA templates removed with 10 U of DNase I (Ambion Inc.) for 25 min at 37° C. The products of transcription were ethanol precipitated and separated on 5% Urea-PAGE. Full-length RNA templates were excised from the gel, eluted at room temperature in 0.3M sodium acetate pH 5.2, 0.03% SDS for 1.5 hr, extracted with phenol/chloroform and ethanol precipitated. The transcripts were dissolved in 50 mM NaCl to a final RNA concentration of 0.1 µg/µl.

Synthesis of $P^{32}$-labeled 254 nt R2 RNA for the gel shift experiments was performed according to the Fermentas Inc. protocol for the synthesis of high specific activity radiolabeled RNA using T7 RNA polymerase. RNA was transcribed from 1 µg of the 254 nt R2 PCR product and DNA template removed by incubation with 2 U of DNase I for 15 min at 37° C. RNA yields after purification from 5% Urea-PAGE were determined by scintillation counting and the known specific activity of labeled nucleotide in the reaction.

TABLE I

Definition of Primer Sequences

| Primer | Nucleotide Sequence | SEQ ID No: |
|---|---|---|
| AB.1 | CTGCAGTAATACGACTCACTATAGGACTTGGGGAATCCGACT | 25 |
| AB.2b | TTTTCATCGCCGGATCATC | 26 |
| AB.8 | GGAAACAGCTATGACCATG | 27 |
| AB.9 | GATGACGAGGCATTTGGCTA | 28 |
| AB.13 | CTGCAGTAATACGACTCACTATAGGTTGAGCCTTGCACAGTAG | 29 |
| AB.17 | CGACGGCCAGTGCCAAGCTTGCATGCCTGCAGGTCGACTCTAGAGGATCC | 30 |
| AB.18 | CGGGATCCGAAGCCAAGGGAGCGAG | 31 |
| AB.19 | GCTCTAGAGCGTACGGCCACGATC | 32 |
| AB.23 | GGGGTACCGACAGGTTTCCCGACTG | 33 |
| AB.25 | GCTCTAGAGTTCCCTTGGCTGTGGT | 34 |
| AB.26 | GCTCTAGAGCAAGCAAGCGCGGGTAAACGGCGGGAGTAACTATGACTCTCTTAA | 35 |
| AB.T7 | TAATACGACTCACTATAG | 36 |
| AB.j44 | AATTCAAGCAAGCGCGG | 37 |
| AB.34 | CGTTCTTCGGGGCGAAAACTC | 38 |

The 334 nt vector RNA was transcribed from the pBSII (SK−) plasmid (Stratagene) predigested with PvuII. The 183 nt vector RNA was transcribed from a template generated from amplification of pBSII(SK−) using primers AB.8 (SEQ ID No: 27, Table I) and AB.T7 (SEQ ID No: 36, Table I). The 600 nt RNA was transcribed like the 334 nt RNA except that a KpnI and BamHI fragment of the R1Dm element (position 5020–5340) was cloned into the polylinker region of pBSII(SK−) (provided by D. Eickbush). The 1090 nt vector RNA was transcribed from pBSII(SK−) predigested with XmmI using T3 RNA polymerase. Finally, the 177 nt donor RNA in FIG. 7 was transcribed from a PCR template using primers AB. I (SEQ ID No: 25, Table I) and AB.9 (SEQ ID No: 28, Table I) and the plasmid pB108 (Xiong and Eickbush, "Functional Expression of a Sequence-specific Reverse Transcription Assays Unless otherwise specified, all RT reactions were performed in 30 µl volumes containing 50 mM Tris-HCl (pH 7.5), 200 mM NaCl, 10 mM $MgCl_2$, 2.5 mM DTT, 0.01% Triton X-100 and 25 µM each dNTP. The concentration of the R2 protein was 0.8–4 nM (3–15 ng). In all TPRT reactions, labeled target DNA (see previous section) was present at a concentration of 6–12 nM (20–40 ng). In most other reactions, 15 µCi of [$\alpha$-$^{32}$P]dCTP 3,000Ci/mmol (New England Nuclear) was added. In the primer extension assays, the DNA oligonucleotides (concentrations as specified in the Figures) were annealed to the RNA by heating to 96° C. and slow cooling (3.5° C./min) to 25° C. For the reactions in FIG. 7, the DNA primer was end-labeled with polynucleotide kinase. End-labeling reactions were performed accordingly to Fermentas Inc. protocol in 20 µl volume containing 200 ng primer and 25 µCi of [γ-$^{32}$P]ATP 3,000Ci/mmol (New England Nuclear). The polynucleotide kinase was inactivated by heating to 96° C. for 10 min. All reverse transcription reaction were incubated at 37° C. for 30–50 min, and stopped by heating at 96° C. for 5 min. Unless otherwise indicated, the excess RNA was removed by digestion with 1–2 µg of RNase A for 10 min at 37° C. and ethanol precipitated before electrophoresis.

Mobility Shift Analysis

RNA gel mobility shift reactions were performed with 10 ng of R2 protein and 10 ng of [$^{32}$P]-labeled 254 nt R2 RNA in a 20 µl reaction mixture containing 50 mM Tris-HCl (pH 7.5), 200 mM NaCl, 10 mM MgCl$_2$, 2.5 mM DTT, 0.01% Triton X-100. The RNA and protein were preincubated at 37° C. for 15 min, placed on ice for 5 min, mixed with 2 µl of loading buffer (0.2% bromophenol blue, 0.02% xylene cyanol FF and 60% glycerol), and analyzed on 5% native polyacrylamide gels containing 5% glycerol (1/55 acrylamide/bisacrylamide). The electrophoresis was performed at 4° C. The identical procedure was applied for the DNA mobility shift assay except that 10 ng R2 protein was preincubated with 20 ng of labeled target DNA.

Analysis of the Junction Sequences Derived from Template Jumps

Unless otherwise indicated the band corresponding to the template jump product was excised from a polyacrylamide gel, eluted with 0.3 M sodium acetate pH 5.2, 0.03% SDS for several hours at room temperature, phenol/chloroform extracted and ethanol precipitated. The isolated cDNA was then used as a template for PCR amplification using the primer indicated in the figure legends. The PCR products were directly cloned into mp18T2 (Burke et al., "R4, a non-LTR Retrotransposon Specific to the Large Subunit rRNA Gene of Nematodes," *Nucleic Acids Res.* 23:4628–4634 (1995), which is hereby incorporated by reference in its entirety) and individual clones sequenced.

Example 1

Recombinant Expression of the *Bombyx mori* R2 Protein

The expression construct, pR260, was derived from construct pR250 (Xiong & Eickbush, *Cell* 55:235–246 (1988), which is hereby incorporated by reference in its entirety). A 3.5 kb SmaI fragment of pR250 from 18 bp upstream of the first methionine codon to the 3' end untranslated region was subcloned into pUC18 in-frame with the lacZ gene. *E Coli* strain JM109/pR260 was grown at 37° C. in LB broth until an OD$_{595}$=0.5–0.6. Isopropylthio-β-galactoside (IPTG) was then added to a final concentration of 0.2 mM and the cultures were further incubated for 1 hour. Cells are harvested by centrifugation, washed in cold 50 mM Tris-HCl, pH 8.0, and collected by centrifugation. The following procedure is described for a 1.5 liters of cells but can be scaled to larger or smaller culture volumes. All procedures are conducted at 0–4° C. The cell pellets are resuspended in 6.8 ml buffer A (0.1 mM Tris-HCl pH7.5, 5 mM EDTA, 50% glycerol) and incubated for 30 minutes in 5 mM dithiothreitol (DTT), 2 mM benzainidine-HCl, and 2 mg/ml lysozyme. 32 ml of buffer B (0.1 M Tris-HCl pH7.5, 1 M NaCl, 5 mM DTT, 0.2% triton X-100, 10 mM MgCl$_2$, 2 mM benzamidine) is then added, followed by an additional 30 minutes incubation. The lysate is centrifuged in a SW50.1 rotor at 33,000 rpm for 20 hours. The upper 1 ml of the supernate from each tube contains little R2 protein and is discarded. The remaining 4 ml of supernate from each tube is decanted and diluted with H$_2$O to lower the NaCl concentration to 0.4 M. The diluted crude extract is loaded onto a 15 ml Q Sepharose-fast-flow column (Pharmacia) equilibrated in 0.4 M NaCl/buffer C (25 mM Tris-HCl pH7.5, 2 mM DTT). The column is washed with 50 ml of the 0.4 M NaCl/buffer C, and the R2 protein eluted with 0.6 M NaCl/buffer C. Fractions containing the R2 endonuclease activity are pooled, dialyzed against 0.2 M NaCl/buffer D (25 mM Tris-HCl pH7.5, 2 mM DTT, 10% Glycerol), and applied to a 1.5 ml DNA-cellulose column (Pharmacia) equilibrated with 0.4 M NaCl/buffer D. The column is washed with 9 ml 0.4 M NaCl/buffer D and eluted with 0.8 M NaCl/buffer D. R2 protein eluted from the DNA cellulose column is concentrated approximately 5-fold on a Centricon-50 column (Amico) and dialyzed against 50% glycerol, 0.4 M NaCl, 25 mM Tris-HCl (pH 7.5) and 2 mM DTT at 4° C. A typical final volume is 100–200 µl of concentrated solution containing from 5–15 ng/µl R2 protein. The protein can be stored after dialysis at −20° C. for several month with only minor decreases in activity.

Protein concentrations were determined on SDS-polyacrylamide gels using the fluorescent stain SYPRO Orange (Bio-Rad Laboratories). The intensity of the R2 band was compared with known concentrations of bovine serum albumin using the fluoroimaging function of a Storm 860 PhosphorImager and Image Quant.

Example 2

RNA Template Jumping After Target-Primed Reverse Transcription

The signature step of the TPRT reaction is the use of the 3' hydroxyl group released by first-strand cleavage of the DNA target site as primer for cDNA synthesis. This cleavage/reverse transcription reaction can be studied in vitro using purified components as shown in FIG. 1. The substrate in the assay is a uniformly P$^{32}$ labeled DNA fragment containing the 28S rRNA gene insertion site. The R2 cleavage site on this substrate is positioned such that a 110 nt fragment is used as the primer. The RNA templates added to the reaction contain the minimum sequences needed to initiate the TPRT reaction: the 3' untranslated region of the R2 element. The R2 RNA templates are either 254 nt in length, if the RNA ends at the precise 3' junction of the R2 element, or 274 nt in length, if the RNA extends 20 nt into the downstream 28S gene sequences.

Denaturing polyacrylamide gel electrophoresis of typical TPRT reactions are shown in FIG. 1B. To allow maximum separation of the TPRT products the small, previously described (Luan et al., "Reverse Transcription of R2Bm RNA is Primed by a Nick at the Chromosomal Target Site: A Mechanism for non-LTR Retrotransposition," *Cell* 72:595–605 (1993), which is hereby incorporated by reference in its entirety) DNA cleavage products have been run off the bottom of the gel. The major TPRT products generated from the 254 nt R2 RNA (lane 1) and the 274 nt R2 RNA (lane 2) are both approximately 365 nt in length because reverse transcription starts at the 3' end of the R2 sequences on the RNA template, irrespective of whether this sequence is located at the 3' end or an internal position of the template (110 nt DNA primer+254 nt RNA template 364 nt) (Luan and Eickbush, "Downstream 28S Gene Sequences on the RNA Template Affect the Choice of Primer and the Accuracy of Initiation by the R2 Reverse Transcriptase,"

Mol. Cell. Biol. 16:4726–4734 (1996), which is hereby incorporated by reference in its entirety). Also visible in both lanes are longer reaction products. A distinct band at 620 nt and a faint band at 870 nt are present in lane 1. The 620 nt product could be formed if the R2 reverse transcriptase, after completing synthesis of the first RNA template, was able to jump to the 3' end of a second RNA template and continue synthesis (110 nt+2×254 nt=618 nt). The faint 870 nt band could be explained by two consecutive jumps (110 nt+3×254 nt 872 nt). In the case of the 274 nt R2 template (lane 2), the longer cDNA products are about 640 and 910 nt. Because the TPRT products generated with the 274 nt R2 RNA are 20 and 40 nt longer than those formed with the 254 nt RNA, the putative jumps between templates would appear to involve the 3' end of the second template, not the internal site used to initiate the TPRT reaction.

To obtain direct support for jumps between RNA templates, the 638 nt cDNA fragment was isolated from lane 2 and the putative jump region of the cDNA was PCR amplified. The sequence of individual cloned products are shown in FIG. 2. All six sequenced junctions revealed that the R2 enzyme had extended to the terminal 5' nucleotide of the first RNA template and continued polymerization at the first 3' nucleotide of the second RNA template. One clone contained a six nucleotide deletion near, but not at the 3' end of the second RNA template. Four of the six junctions had an additional nucleotide between the two RNA sequences. These extra nucleotides could have been added by the R2 reverse transcriptase during the jump between templates. A similar addition of non-templated nucleotides has previously been observed when the R2 reverse transcriptase initiates the TPRT reaction (Luan et al., "Reverse Transcription of R2Bm RNA is Primed by a Nick at the Chromosomal Target Site: A Mechanism for non-LTR Retrotransposition," *Cell* 72:595–605 (1993); and Luan and Eickbush, "RNA Template Requirements for Target DNA-Primed Reverse Transcription by the R2 Retrotransposable Element," *Mol. Cell. Biol.* 15:3882–3891 (1995), each of which is hereby incorporated by reference in its entirety). The extra nucleotides could also have been generated during the in vitro synthesis of the RNA template. T7 RNA polymerase has been shown to add an additional residue (usually A) in DNA run-off reactions similar to those employed to generate RNA templates (see Millagan and Uhlenbeck, "Synthesis of Small RNAs using T7 RNA Polymerase," *Meth. Enzymol.* 180:51–62 (1989), which is hereby incorporated by reference in its entirety).

Reverse transcription of the terminal nucleotides of the donor and acceptor RNAs eliminates the possibility that the jumps between RNA templates are promoted by annealing of the 5' end of the newly synthesized cDNA to the acceptor RNA template. Furthermore, initiation of reverse transcription at the terminal 3' nucleotide of the 274 nt acceptor RNA template, rather than 20 nucleotides internally, suggests an important role of free 3' ends rather than the RNA secondary structure (Mathews et al., "Secondary Structure Model of the RNA Recognized by the Reverse Transcriptase from the R2 Retrotransposable Element," *RNA* 3:1–16 (1997), which is hereby incorporated by reference in its entirety) in the template jumping reaction. These properties of the R2 reverse transcriptase are in sharp contrast to the strand transfers which occur in the reverse transcription cycles of retroviruses and LTR-retrotransposons.

The R2 reverse transcriptase, at least under the in vitro condition described here, cannot efficiently use the 3' end of a RNA:DNA hybrid to initiate reverse transcription. Therefore, the template jumps in FIG. 1B appear to involve the ability of the actively elongating R2 reverse transcriptase to associate with the 3' end of a second RNA template before it dissociates from the first RNA template. This reaction can thus be viewed as continuous cDNA synthesis on non-continuous RNA templates.

If it is assumed that the R2 enzyme, upon reaching the 5' end of the first RNA template, has only limited time to bind another RNA template before it dissociates, then one would predict that the frequency of the template jumps would be dependent upon the concentration of free RNA ends in the reaction. Therefore, a series of reactions were conducted where the concentration of the 254 nt RNA template was incrementally increased. The frequency of the template jumps (618 nt fragment) relative to the total TPRT products over a 100 fold range in RNA concentration was plotted in FIG. 3. As predicted, the frequency of template jumping increased as the concentration of RNA increased. At the highest concentration of RNA tested, 40 nM, approximately 13% of the TPRT reactions underwent a template jump.

Example 3

RNA Priming of the Reverse Transcription Reaction

Figure 4:
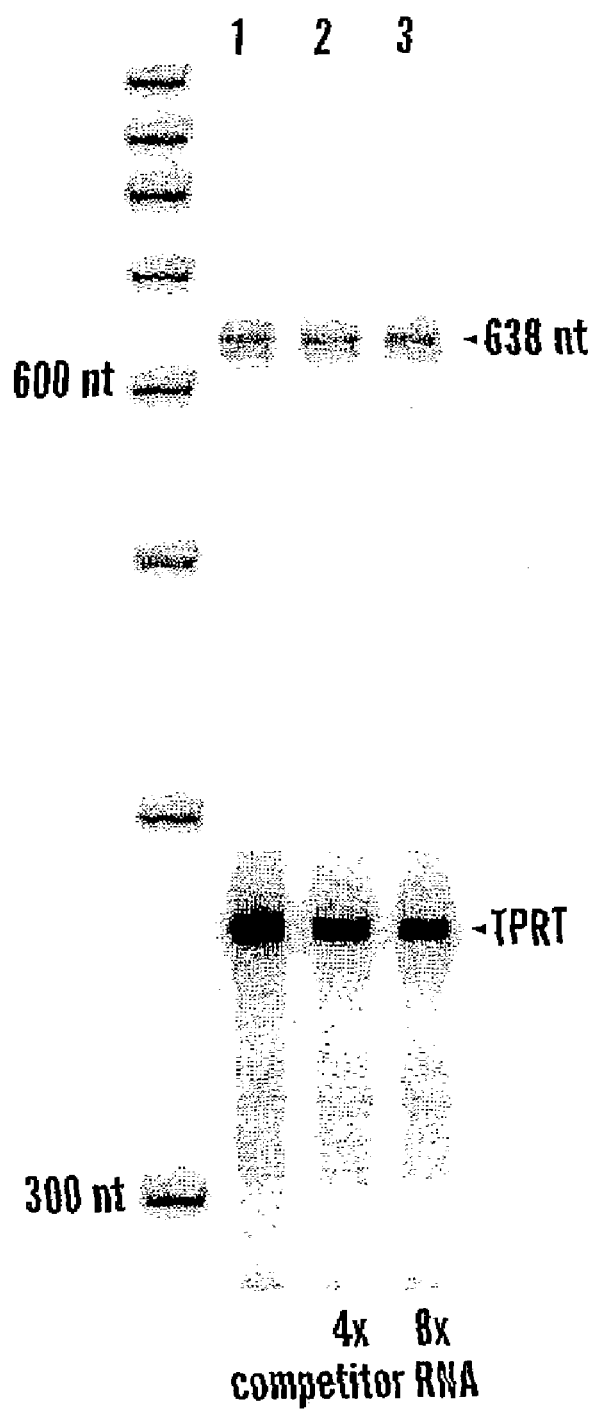
FIG. 4 is an image of an autoradiograph which illustrates that template jumps during the TPRT reaction are specific to R2 RNA templates. The reactions were conducted as in FIG. 1 except that the RNA templates added to the reactions were: lane 1, 50 ng of the 274 nt R2 RNA (20 nM); lane 2, 20 nM 274 nt R2 RNA and 80 nM 334 nt vector RNA; lane 3, 20 nM 274 nt R2 RNA and 160 nM 334 nt vector RNA. The competing vector RNA would give rise to TPRT products of about 445 nt. Template jumps of the major TPRT product to vector RNA would give rise to a ~700 nt band.

To determine if there is specificity for the RNA used as acceptor in the template jump, the TPRT assays were also conducted in the presence of an excess of non-R2 competitor RNA. The 334 nt competitor RNA was a transcript of the pBSII(SK−) plasmid. It has previously been shown that only those RNAs that contain the 3' untranslated region of the R2 element can be used as templates in the TPRT reaction (Luan and Eickbush, "RNA Template Requirements for Target DNA-primed Reverse Transcription by the R2 Retrotransposable Element," *Mol. Cell. Biol.* 15:3882–3891 (1995), which is hereby incorporated by reference in its entirety). This specificity was confirmed in FIG. 4, as the only initial TPRT product observed was the approximately 365 nt fragment generated from the R2 RNA template. TPRT products generated from the longer vector RNA would be approximately 445 nt in length. In a similar manner, the only products resulting from template jumps between RNAs were approximately 640 nt and 910 nt in length (compare lanes 1 and 3), indicating that only the R2 RNA was being used as acceptor of the jump even in the presence of an 8 fold molar excess of the competitor RNA.

Example 4

Reverse Transcription in the Absence of DNA Target Site

Figure 5A:
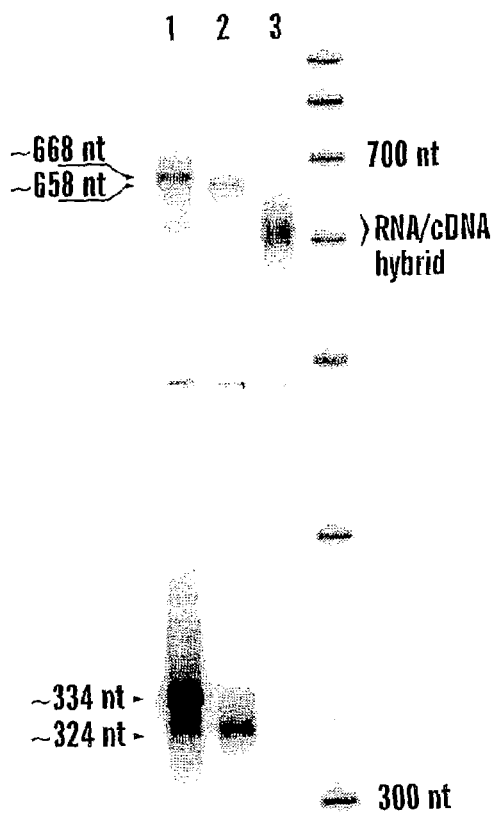
FIGS. 5A–B illustrate how reverse transcription can be primed by RNA itself.
Figure 5B:
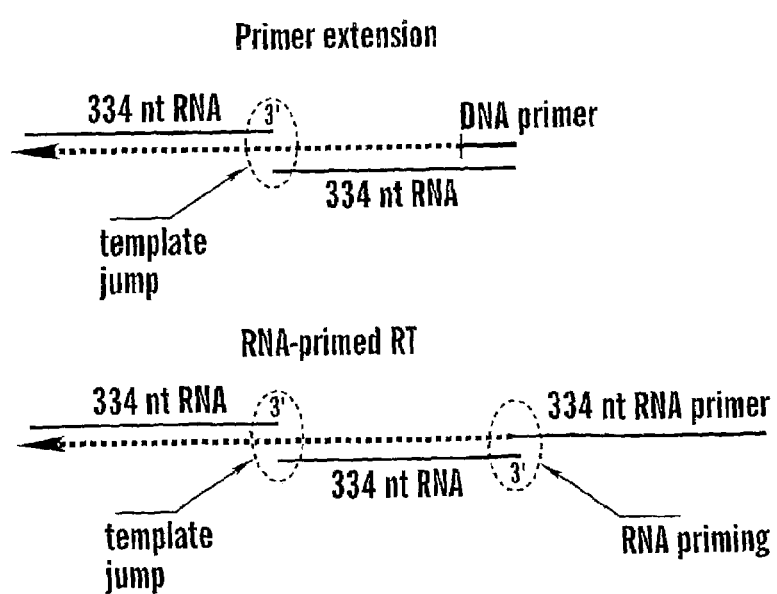

It was determined whether the R2 enzyme could undergo template jumps during reverse transcription reactions that are primed by a non-specific method of annealing a short DNA oligonucleotide to an RNA template (FIG. 5B). In such primer extension assays, both R2 and non-R2 RNA can be used by the R2 reverse transcriptase as templates (Luan et al., "Reverse Transcription of R2Bm RNA is Primed by a Nick at the Chromosomal Target Site: A Mechanism for non-LTR Retrotransposition," *Cell* 72:595–605 (1993), which is hereby incorporated by reference in its entirety). An extension assay using a DNA oligonucleotide annealed to the 20 nt at the 3' end of the 334 nt vector RNA is shown in FIG. 5A, lane 1. As expected the major cDNA product was 334 nt in length corresponding to simple extension by the reverse transcriptase to the end of the vector RNA. Also produced was a cDNA fragment approximately 670 nt, the length expected for reverse transcription of two consecutive RNA molecules. Thus, in the absence of the DNA target and R2 RNA, the R2 reverse transcriptase can also undergo template jumps between vector RNA sequences.

During analysis of these primer extension assays, it was noticed that the synthesis of cDNA was not completely dependent upon the presence of a DNA primer annealed to the RNA template. Approximately 20% of the cDNA synthesis could be generated without a primer, suggesting an alternative means of priming reverse transcription. It has previously been shown that under conditions of a TPRT reaction, the R2 protein can use the 3' end of a second RNA molecule to prime reverse transcription (Luan and Eickbush, "Downstream 28S gene Sequences on the RNA Template Affect the Choice of Primer and the Accuracy of Initiation by the R2 Reverse Transcriptase," *Mol. Cell. Biol.* 16:4726–4734 (1996), which is hereby incorporated by reference in its entirety). Sequence analysis of the products of these reactions indicated that the 'primer' RNA had not annealed to the R2 'template' RNA (Luan and Eickbush, "Downstream 28S gene Sequences on the RNA Template Affect the Choice of Primer and the Accuracy of Initiation by the R2 Reverse Transcriptase," *Mol. Cell. Biol.* 16:4726–4734 (1996), which is hereby incorporated by reference in its entirety). Here, it is shown that elimination of both the DNA target and R2 RNA from the reaction enables the protein to conduct this RNA-priming with non-specific RNA templates (diagramed in FIG. 5B).

Results of an RNA-primed reverse transcription reaction using the 334 nt vector RNA template is shown in FIG. 5A, lanes 2 and 3. In lane 2, the reaction products have been treated with RNase A before separation on the polyacrylamide gel, while the reaction products in lane 3 have not been treated with RNase A. In lane 3, the major product was a diffuse band slightly larger than 600 nt. After treatment with RNase A the products were reduced to a major band at approximately 324 nt with faint bands extending up to 334 nt. This reduced length of the cDNA products compared to lane 1 indicated that the preferred site of initiation of reverse transcription in the RNA-primed reaction was about 10 nt from the 3' end of the RNA template. The presence of a 660 nt cDNA product in lane 2 indicated that the R2 enzyme can also undergo template jumps in these RNA-primed reactions.

Example 5

RNA Preferences in the Absence of the DNA Target Site

Figure 6A:
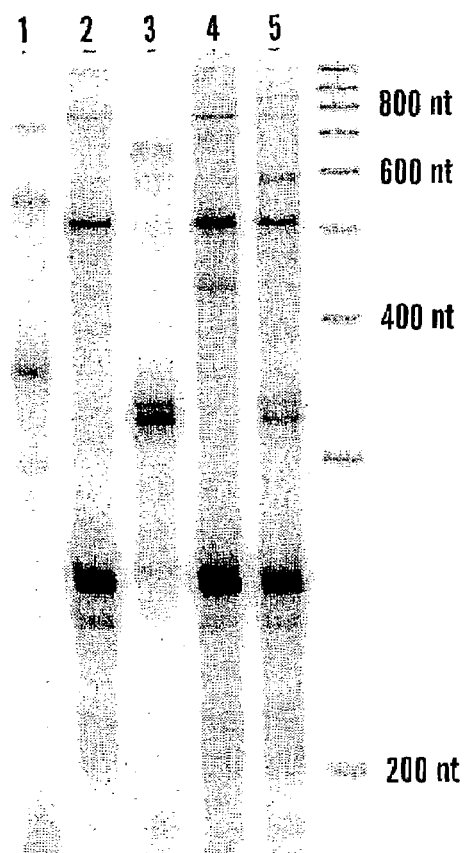
FIGS. 6A–B illustrate the specificity of the RNA-primed reverse transcription and template jumping reactions.

In FIG. 6, the efficiency of RNA-primed reverse transcription and template jumping are compared between three RNAs: a 183 nt non-R2 RNA derived from pBSII(SK–), the 254 nt R2 RNA, and 334 nt vector RNA. Reverse transcription was primed by the RNAs themselves (no DNA primers), and all products were digested with RNase A to remove these RNA primers before electrophoresis. In the case of the short vector RNA (lane 1), the initial cDNA products were approximately 180 nt in length, which is consistent with reverse transcription starting near the 3' end of the RNA template. Template jumping was highly efficient with this RNA as cDNA fragments of 360, 540, 720 and 900 nt were generated representing one, two, three, and four consecutive template jumps. With the R2 RNA template (lane 2), the major cDNA fragments were about 250 nt, consistent with reverse transcription starting near the 3' end of the RNA template, while a faint band approximately 15 nt shorter than the major band suggested cDNA synthesis also initiated at a more internal site. One, two, and three template jumps were seen with the R2 RNA template. In the case of the 334 nt vector RNA, priming of cDNA synthesis occurred at several sites near the 3' end of the RNA, and both single and double template jumps were detected (660 and 1000 nt fragments).

The relative efficiency of the initial RNA-primed reverse transcription reaction and of the template jumps for each of the three RNAs are compared in Table II (below). The efficiency of the initial RNA-primed reverse transcription step was highest with the R2 RNA template and lowest for the 334 nt RNA. The frequency of template jumps once reverse transcription initiated was 13–15% with the 254 and 183 nt RNA, but only 4% with the 334 nt RNA.

TABLE II

RNA Specificity of the RNA-primed Reverse Transcription Assay

| RNA template | Frequency of RNA-primed RT | Template Jumps |
| --- | --- | --- |
| 254 nt (R2 RNA) | 1.00 | 12.9% |
| 183 nt (vector RNA) | 0.70 | 15.1% |
| 334 nt (vector RNA) | 0.44 | 3.9% |
| 254 nt + 183 nt - - - 254 nt | 1.59 | 10.9% |
| 254 nt + 183 nt - - - 183 nt | 0.17 | 2.1% |
| 254 nt + 334 nt - - - 254 nt | 0.86 | 10.1% |
| 254 nt + 334 nt - - - 334 nt | 0.14 | 0.7% |

All values are derived from the data in FIG. 6. Values for the RNA-primed reverse transcription represent the combination of all RNA-unit-length bands visible in the lane and are given as a fraction relative to that supported by R2 RNA alone. The frequency of template jumps are given as percentages of the total reverse transcripts that have undergone a template jump and is the combined values for all jumps (single, double, etc. corrected for thelength of the cDNA fragment). Values for the template jumps in the competition reactions represent only those between similar templates (i.e. 254 nt to 254 at jumps), and do not include the hybrid bands (i.e. 430 nt in lane 4 and 590 in lane 5) as it is uncertain which RNAs were the donors and acceptors in these jumps.

Lanes 4 and 5 of FIG. 6 are the cDNA products of competition experiments between equal molar ratios of the R2 RNA and the individual vector RNAs. In the case of the 183 nt and 254 nt competition, the significant reduction in intensity of the 180 nt band and the increased intensity of the 250 nt band indicated that the R2 RNA was the preferred template in the RNA-priming reaction. In the case of the 254 nt and 334 nt competition, reverse transcription of R2 RNA was again preferred over the longer vector RNA (lane 5). Thus, RNA-primed cDNA synthesis occurred more readily with the R2 RNA template than with either the shorter or longer vector RNAs. However, stimulation of cDNA synthesis from the R2 RNA by the addition of the 183 nt RNA (Table 2), suggested the short vector RNA functioned more efficiently than the R2 RNA in priming reverse transcription of the R2 template.

The competition experiments in FIG. 6 also suggested that template jumping occurred preferentially to the R2 template. In both lanes 4 and 5, the template jumps between R2 RNAs (fragments at 500 and 750 nt) were only slightly reduced compared to that in lane 3. Meanwhile, the levels of vector RNA to vector RNA jumps in lane 4 (360 nt) and lane 5 (664 nt) were reduced from 5 to 7 fold (see Table 1). Most jumps from the vector RNAs appear to have gone to the R2 RNA as hybrid products (430 nt in lane 4, and 590 nt in lane 5) were readily apparent in both lanes. These results indicate that even in the absence of the R2 RNA template, the R2 protein can undergo RNA-primed reverse transcription and template jump with non-R2 RNA templates. However, the R2 protein prefers to initiate reverse transcription on the R2 RNA as well as use R2 RNA as the acceptor of template jumps.

Figure 6B:
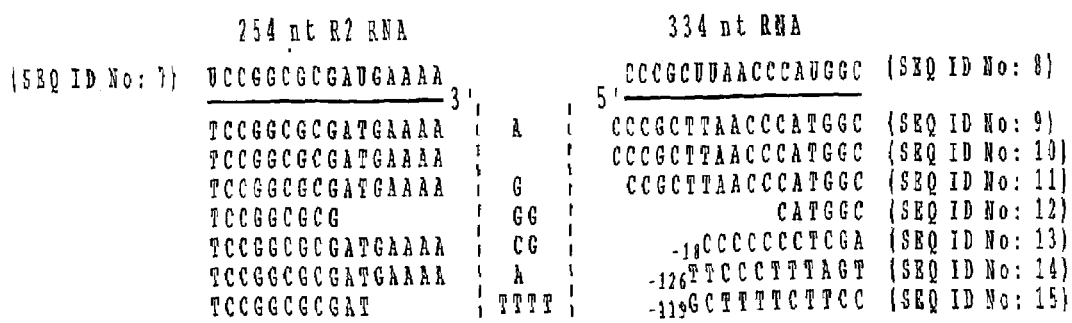

To affirm that these template jumps in the RNA-primed reactions occurred without annealing of the cDNA to the acceptor RNA template, the cDNA region corresponding to a 334 nt donor to 254 nt acceptor template jump was PCR amplified from the total reaction products of lane 5. The total reaction products were used in the amplification rather than the purified 590 nt hybrid in order to sample the many faint products visible in FIG. 6A that are not of unit RNA length (i.e., cannot be attributed to any combination of 254 and 334 nt RNAs). As shown in FIG. 6B, in five of the seven sequenced junctions, the template jump occurred to the terminal 3' nucleotide of the acceptor R2 RNA. In the two remaining cases, the jumps were to sites 5 and 7 nucleotides from the 3' end, but in neither case did the jump involve sequences that would enable the cDNA made from the 334 nt RNA to anneal to the R2 RNA. Several of the junctions also represented reverse transcription reactions that did not proceed to the 5' end of the 334 nt vector RNA. These premature jumps can explain many of the faint product bands seen on gels, however it is not clear what fraction of these products were a result of RNA degradation, and what fraction represented template jumps before the reverse transcriptase reached the end of the first template.

Example 6

Directing Template Jumps Between RNA's

Figure 7A:
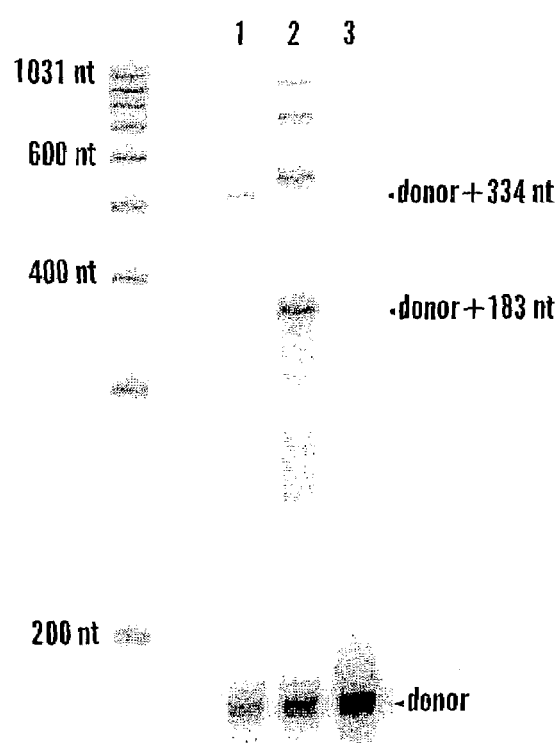
FIGS. 7A–B illustrate the affects of directed template jumps between 'donor' and 'acceptor' RNA templates.

Increasing the ratio of DNA oligonucleotides used to anneal to the 3' end of an RNA template will block this RNA from being an acceptor of a template jump. As shown in FIG. 7A (lane 3), using a 6-fold molar excess of primer to RNA template (three times higher than used in FIG. 5, lane 1) resulted in the synthesis of full-length cDNA products (~177 nt), but no template jumps. Template jumps were readily observed if a second RNA template, that did not anneal to the DNA primer, was added to the reaction. In lane 2, the addition a the 183 nt vector RNA resulted in nearly 40% of the cDNA undergoing a template jump (many underwent multiple consecutive jumps). In lane 1, the addition of the 334 nt vector RNA resulted in about 6% of the cDNA undergoing a template jump.

Figure 7B:
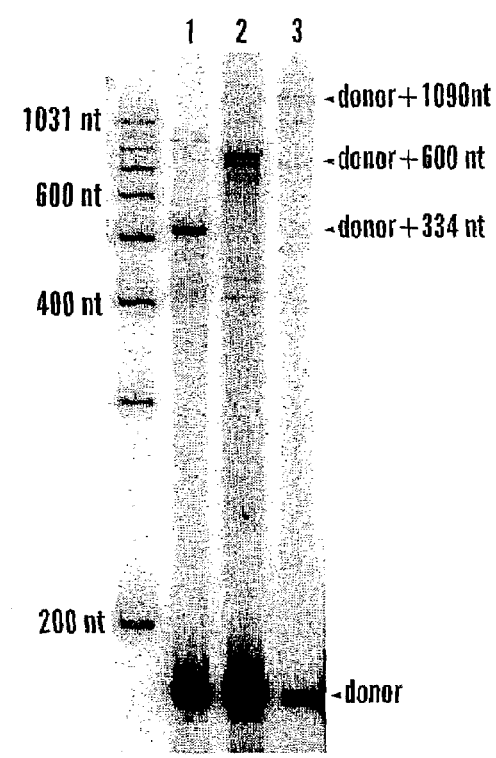

FIG. 7B shows the relative efficiency of directed template jumps between the donor RNA and even longer RNAs (334 nt, 600 nt and 1090 nt). The nature of these three RNAs are described above. While template jumps onto each of these RNAs were observed, the relative efficiencies of these jumps varied as did the efficiency of the initial primer extension reaction itself. The reduction in efficiency of the primer extension reaction with different RNAs is possibly a result of the preference of the R2 protein to bind certain RNAs and, thus, to reduce its ability to bind the donor RNA. Meanwhile the general decrease in the efficiency of the template jumps with longer RNAs is likely to be a mass affect in which the R2 protein is more likely to encounter the 3' end of a shorter RNA compared to the 3' end of a longer RNA.

Example 7

Figure 3:
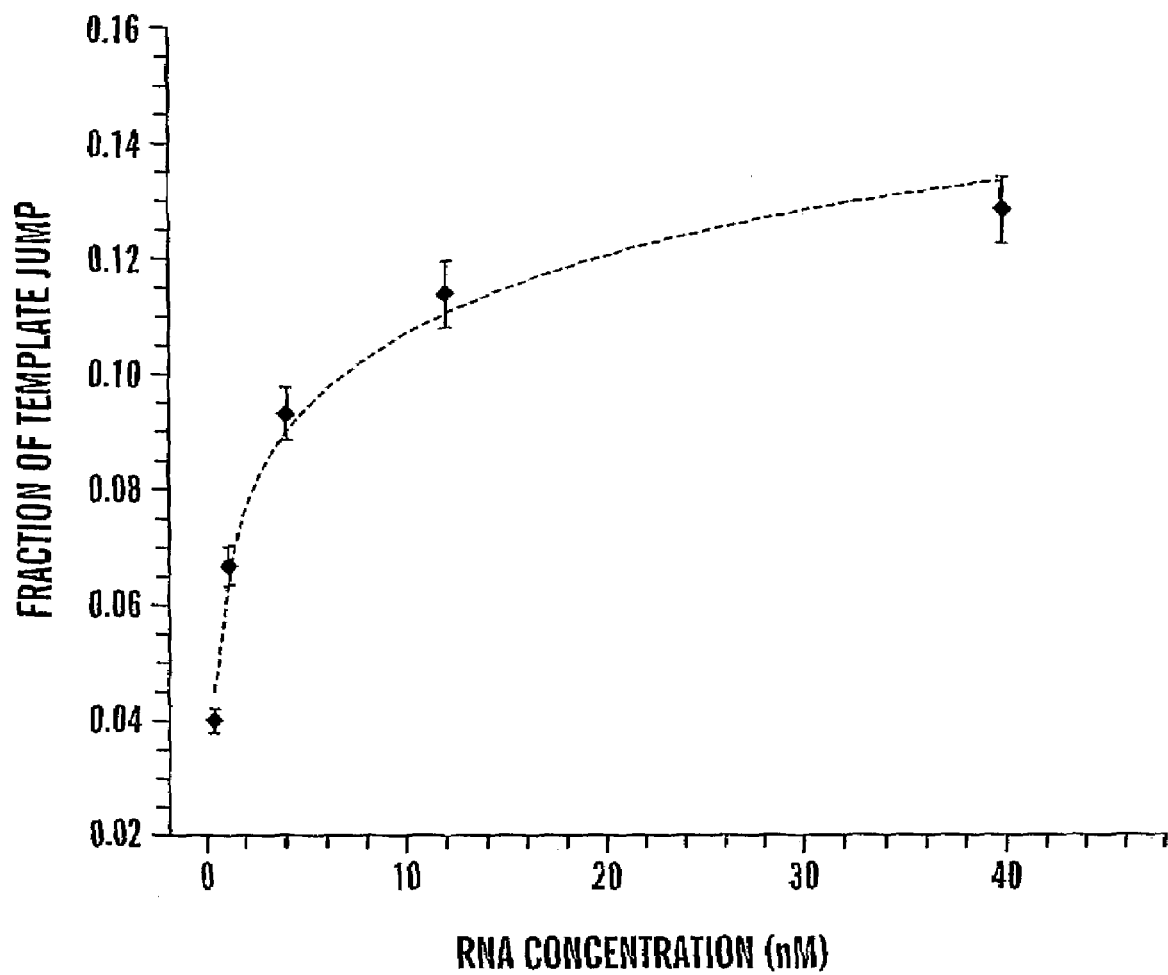
FIG. 3 is a graph illustrating the effects of RNA concentration on the efficiency of the template jumping reaction. TPRT reactions were performed similar to that in FIG. 1 with the 254 nt R2 RNA template concentration varied from 0.4–40 nM. Products of TPRT reactions were separated on a 6% denaturing polyacrylamide gel and the intensity of the 618 nt fragment was determined relative to the total level of TRPT (~364 and ~618 nt bands) using a PhosphorImager and Image Quant.
Figure 8A:
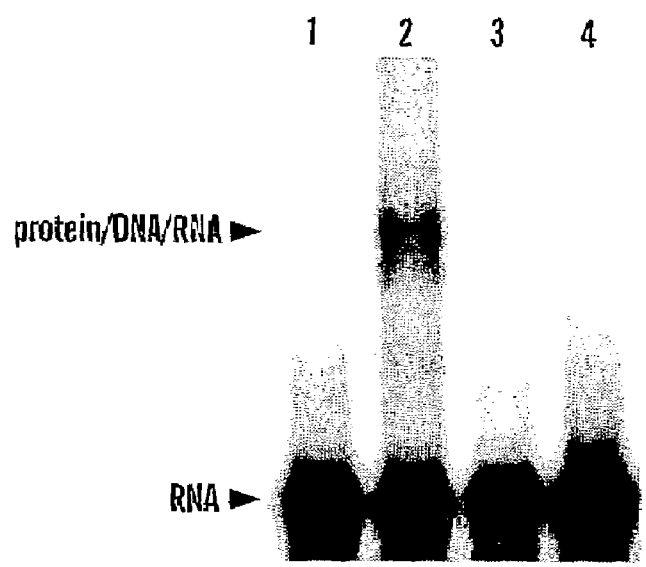
FIGS. 8A–B illustrate the affect that the DNA target has to stabilize interactions between the R2 protein and its RNA template. All components were preincubated for 15 minutes at 37° C. and separated on 5% native polyacrylamide gels at 4° C.

The DNA Target Site Stabilizes Interactions Between the R2 Protein and its Template While R2 RNA templates are preferred, vector RNAs (or any non-R2 RNAs) can compete as templates in RNA-primed reverse transcription reactions as well as acceptors in template jumps between RNAs. This contrasts with the activity of the R2 protein in the presence of the target DNA, in which only R2 RNAs can be used as templates in the target DNA-primed or RNA-primed reverse transcription reactions (Luan and Eickbush, "Downstream 28S Gene Sequences on the RNA Template Affect the Choice of Primer and the Accuracy of Initiation by the R2 Reverse Transcriptase," *Mol. Cell. Biol.* 16:4726–4734 (1996); and Mathews et al., "Secondary Structure Model of the RNA Recognized by the Reverse Transcriptase from the R2 Retrotransposable Element," *RNA* 3:1–16 (1997), each of which is hereby incorporated by reference in its entirety), as well as acceptors of template jumps (FIG. 3). These results suggest that when the R2 protein is bound to DNA it has more specific structural requirements for the RNA used as template, which in turn might mean a higher affinity of the protein for the R2 RNA. Direct evidence for an increased affinity of the R2 protein for binding the R2 RNA in gel mobility shift assays is demonstrated below. As shown in FIG. 8A, R2 protein and labeled R2 RNA incubated in the absence of DNA do not generate a gel shift under the conditions of these reactions (lane 1); however a shifted complex is readily observed if the DNA target is added to the incubation (lane 2). Similar complexes are not observed in the presence of single-stranded DNA (lane 3) or in the presence of double-stranded DNAs not corresponding to the target site (lane 4).

Figure 8B:
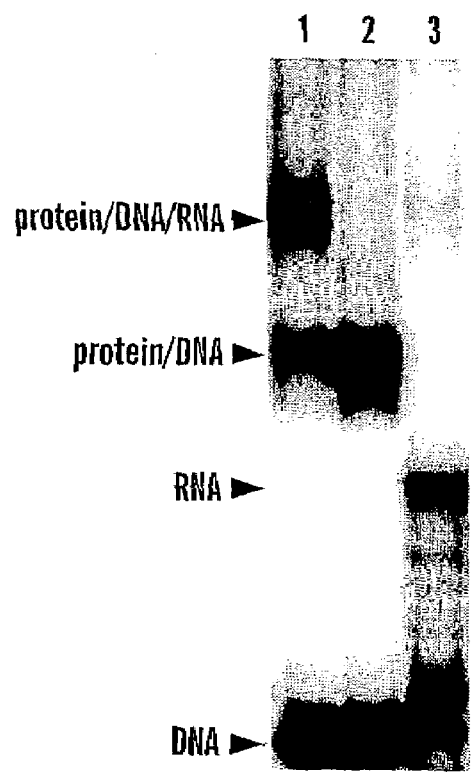

To confirm that the shifted complex in FIG. 8A is indeed a complex of RNA, protein, and DNA, the mobility shift assays were also conducted in the presence of labeled DNA target (FIG. 8B). In the presence of the R2 protein and the DNA target, a shifted complex is observed (lane 2). If R2 RNA is added to the protein and target DNA, then a further reduction in the mobility of the complex (a supershift) is observed (lane 1). The mobility of this RNA:protein:DNA complex is the same whether the DNA is labeled (FIG. 8B, lane 1) or the RNA is labeled (FIG. 8A, lane 2 and FIG. 5B lane 3). These results demonstrate that the DNA target site increases the specific interactions between the R2 protein and R2 RNA. In the absence of DNA, only less stable interactions are possible between the R2 protein and its RNA template, which can explain why vector RNA can substitute for R2 RNA in the reverse transcription reactions conducted in the absence of target DNA.

Example 8

Template Jumps onto Single-Stranded DNA

The ability of the R2 protein to template jump onto another RNA would suggest that the protein may also be able to template jump onto single stranded DNA. Surprisingly, such jumps have only been observed when R2 RNA is being used as the initial template. As shown in FIG. 9, increasing concentrations of a 19 nt DNA primer complementary to the 3' end of the 254 nt R2 RNA template (lanes 1–3) inhibited template jumping to the R2 RNA itself, similar to that shown above for vector RNA templates (FIG. 7). However, with the R2 template a new series of cDNA products were generated approximately 20, 40 and 60 nt longer than the R2 RNA template. As shown below, these new products were template jumps onto the excess DNA oligonucleotide primers in the reaction. Such template jumps to DNA oligonucleotides were not observed with the donor RNA template in FIG. 7.

To determine if the R2 protein has sequence or length preference for these templates jumps to ssDNA, two longer ssDNA were tested. One ssDNA corresponded to a 50 nt segment from the pBSII(SK−) plasmid (FIG. 9A, lane 4), while a second 54 nt ssDNA corresponded to the sequence of the 28S gene immediately upstream of the R2 insertion site (lane 5). This latter ssDNA was tested because it has previously been postulated that the R2 element may complete the R2 integration reaction by jumping onto these upstream 28S gene sequences and continuing synthesis (Burke et al., "The Domain Structure and Retrotransposition Mechanism of R2 Elements are Conserved Throughout Arthropods," *Mol. Bio. Evol.* 16:502–511 (1999), which is hereby incorporated by reference in its entirety). Template jumps to both of these ssDNA were readily observed. Based on the lengths of the reaction products, the jumps occurred to locations near the 3' end of these oligonucleotides.

Figures 9A, 9B:
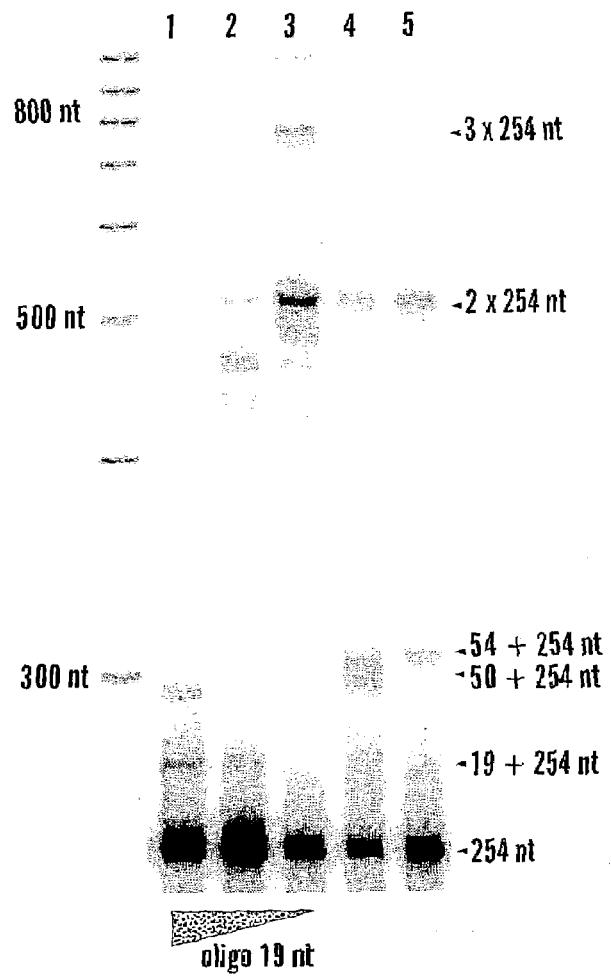
FIG. 9A is an autoradiograph which illustrates that template jumps can occur onto single-stranded DNA. Each reverse transcription reaction contained 150 ng 254 nt R2 RNA pre-annealed with various amounts of the DNA primer AB.2b (19 nt) (SEQ ID No: 26, Table I). Lane 1, 500 ng primer AB.2b (SEQ ID No: 26, Table I); lane 2, 50 ng primer AB.2b (SEQ ID No: 26, Table I); lane 3, 5 ng primer AB.2b (SEQ ID No: 26, Table I); lane 4, 50 ng primer AB.2b (SEQ ID No: 26, Table I)+250 ng ssDNA AB.17 (SEQ ID No: 30, Table I) (50 nt); lane 5, 50 ng primer AB.2b (SEQ ID No: 26, Table I)+250 ng ssDNA AB.26 (SEQ ID No: 35, Table I) (54 nt).
FIG. 9B illustrates the junction sequences of template jumps from the 254 nt R2 RNA to the 54 nt ssDNA. The ~310 nt band in lane 5 (panel A) was excised from the gel, the DNA eluted and PCR amplified using primers AB.23 (SEQ ID No: 33, Table I) and AB.2b (SEQ ID No: 26, Table I). The PCR products were cloned and random clones sequenced. Shown at the top is the 3' end of the 54 nt ssDNA acceptor (SEQ ID No: 16) and the 5' end of the 254 nt R2 RNA donor (SEQ ID No: 17). Below these sequences are the five sequenced junctions, two of which were identical (SEQ ID No: 18). Three of the sequences (SEQ ID Nos: 19–21) possessed junctions that contain additional nucleotides not derived from either of the donor RNA or acceptor ssDNA (nucleotides between the dotted vertical lines).

To obtain direct evidence for the use of ssDNA as an acceptor of template jumps, the 300–310 nt reverse transcription products from the reaction in lane 5 were excised and PCR amplified using one primer within the 54 bp extension and a second primer within the R2 sequence. The sequence of individual clones are shown in FIG. 9B. In most cases, the RT extended to the 5' end of the R2 RNA template and then jumped to the terminal 3' nucleotide of the ssDNA. In two cases, the jump occurred to positions 2 and 9 nt from the 3' end of the primer. While these could represent jumps to internal positions of the ssDNA, it has been have found that the R2 endonuclease has single-stranded 3' exonuclease activity. Thus, many of these jumps to apparent internal locations near the end of the oligonucleotide may be jumps to the 3' end of a partially degraded ssDNA template. As was seen with the template jumps from RNA to RNA, these RNA to ssDNA templates jumps also contained additional, non-templated nucleotides.

Example 9

Retroviral Reverse Transcriptases are Unable to Jump Templates

Figure 10:
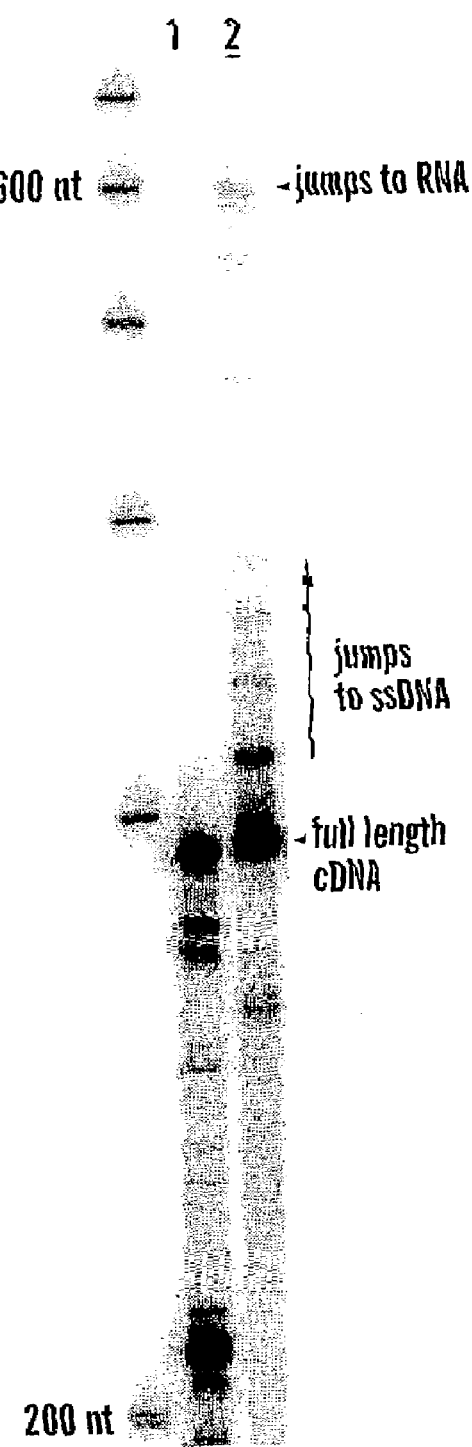
FIG. 10 is an image of an autoradiograph which illustrates a comparison of the template jumping activity of the R2 and AMV RTs. The reactions contained 150 ng of a 283 nt R2 RNA pre-annealed with 250 ng DNA primer AB.2b (SEQ ID. No: 26, Table I). Reactions were conducted in the identical conditions except that lane I contained 5 U of AMV RT (Promega) and lane 2 contained 10 ng of R2 protein.

All of the reactions that have been conducted with the R2 protein herein have also been conducted using commercially available retroviral RTs. Consistent with many previous studies (see Coffin et al., *Retroviruses*, Cold Spring Harbor Press, Cold Spring Harbor, N.Y. (1997), which is hereby incorporated by reference in its entirety), these retroviral enzymes were unable to conduct RNA-primed reverse transcription and template jumps to either RNA or ssDNA templates. FIG. 10 is an example of such a comparison in which an R2 RNA template has been primed with a short oligonucleotide. Full-length cDNA products were seen with the R2 reverse transcriptase, as well as jumps to the DNA oligonucleotide and RNA template (lane 2). In contrast, under identical conditions the longest products generated by the AMV RT were only full-length reverse transcripts of the RNA template (lane 1). The greater abundance of shorter cDNA products seen with the retroviral enzyme was a reflection of the reduced ability of the AMV RT to extend to the 3' end of an RNA template compared to the R2 enzyme.

Based on the evidence provided in Examples 2–9, it is evident that the R2 protein or polypeptide possess two unusual properties.

First, the R2 RT can jump between RNA templates. The cDNA strand from these jumps frequently contain the terminal nucleotides of the donor and acceptor RNA molecules indicating that these jumps do not involve annealing of the newly formed cDNA strands to the acceptor RNA template. Thus, the R2 protein can conduct continuous cDNA synthesis on non-continuous RNA templates. In contrast, strand transfer by retroviral RTs requires sequence identity between the donor and acceptor RNA templates (Peliska and Benkovic, "Mechanism of DNA Strand Transfer Reactions Catalyzed by HIV-1 Reverse Transcriptase," *Science* 258:1112–1118 (1992); and DeStefano et al., "Requirements for Strand Transfer Between Internal Regions of Heteropolymer Templates by Human Immunodeficiency Virus Reverse Transcriptase," *J. Virol.* 66: 6370–6378 (1992), each of which is hereby incorporated by reference in its entirety). Retroviral transfers are accomplished through catalytic removal of the donor RNA from the cDNA strand by an associated RNase H domain which allows the cDNA to anneal to the acceptor RNA molecule. The R2 RT has no RNase-H domain (Malik et al., "The Age and Evolution of non-LTR Retrotransposable Elements," *Mol. Biol. Evol.* 16:793–805 (1999), which is hereby incorporated by reference in its entirety), and no such activity has been detected in vitro (Luan et al., "Reverse Transcription of R2Bm RNA is Primed by a Nick at the Chromosomal Target Site: A Mechanism for non-LTR Retrotransposition," *Cell* 72:595–605 (1993), which is hereby incorporated by reference in its entirety). The only similarity between the jumps by the R2 and retroviral RTs is that both enzymes can add non-templated nucleotides to the cDNA at the end of the donor RNA template (Peliska and Benkovic, "Mechanism of DNA Strand Transfer Reactions Catalyzed by HIV-1 Reverse Transcriptase," *Science* 258:1112–1118 (1992), which is hereby incorporated by reference in its entirety). In the cause of the retroviral mechanism, these extra nucleotides leads to hypermutability in the template switch region of the genome. As will be described below, template jumping by the R2 protein may explain the high sequence variation at the 5' junction of R2 elements.

A second unusual property of the R2 RT is that it can use the 3' end of a second RNA molecule to initiate reverse transcription. Such RNA-primed reactions have been previously characterized as an alternative to the TPRT reaction when the R2 protein was bound to the DNA target site (Luan and Eickbush, "Downstream 28S Gene Sequences on the RNA Template Affect the Choice of Primer and the Accuracy of Initiation by the R2 Reverse Transcriptase," *Mol. Cell. Biol.* 16:4726–4734 (1996), which is hereby incorporated by reference in its entirety). Similar to the TPRT reaction itself, RNA-priming did not require the annealing of the primer RNA to the template RNA (Luan and Eickbush, "Downstream 28S Gene Sequences on the RNA Template Affect the Choice of Primer and the Accuracy of Initiation by the R2 Reverse Transcriptase," *Mol. Cell. Biol.* 16:4726–4734 (1996), which is hereby incorporated by reference in its entirety). It was shown above that when the R2 protein is not bound to the DNA target, any RNA can be reverse transcribed from its 3' end by this RNA-priming reaction. RNA-priming without the annealing of the primer RNA to the template RNA has not been observed for retroviral RT. However, the RT encoded by the Mauriceville mitochondrial retroplasmid of *Neurospora crassa* has been shown capable of using the 3' ends of single-stranded DNA to prime reverse transcription in the absence of significant sequence identity (Wang et al., "The Mauriceville Plasmid of *Neurospora crassa*: Characterization of a Novel Reverse Transcriptase that Begins cDNA Synthesis at the 3' End of Template RNA," *Mol. Cell. Biol.* 12:5131–5144 (1992); and Kennell et al., "The Mauriceville Plasmid of *Neurospora* spp. Uses Novel Mechanisms for Initiating Reverse Transcription in vitro," *Mol. Cell. Biol.* 14:3094–3107 (1994), each of which is hereby incorporated by reference in its entirety).

The different properties of the R2 and retroviral RTs is perhaps not unexpected because these enzymes differ substantially in size and are highly divergent in sequences (Xiong and Eickbush, "Origin and Evolution of Retroelements Based on their Reverse Transcriptase Sequences," *EMBO J.* 9:3351–3362 (1990), which is hereby-incorporated by reference in its entirety). Indeed, it is easier to align the amino acid sequence of the RT domains of R2 and other non-LTR retrotransposons with the comparable domains of mitochondrial group II introns and retroplasmids, bacterial msDNA and even telomerase than it is to the retroviral and LTR retrotransposon domains (Eickbush, "Origin and Evolutionary Relationships of Retroelements," *In The Evolutionary Biology of Viruses* (Morse, S. S. ed.), pp. 121–157, Raven Press, New York (1994); and Nakamura et al., "Telomerase Catalytic Subunit Homologs from Fission Yeast and Human," *Science* 277:955–959 (1997), each of which is hereby incorporated by reference in its entirety). As a result the phylogenetic relationship of these various retroelements can be established with some confidence, while the relationship of these elements to the retroviruses and LTR retrotransposons remains controversial (Nakamura and Cech, "Reversing Time: Origin of Telonmerase," *Cell* 92:587–600 (1998); and Malik and Eickbush, "Phylogenetic Analysis of Ribonuclease H Domains Suggests a Late, Chimeric Origin of LTR Retrotransposable Elements and Retroviruses," *Genome Res.* 11: 1187–1197 (2001), each of which is hereby incorporated by reference in its entirety).

The R2 RT also shares with the other retroelement RTs the ability to specifically bind the RNA that will be used as template for cDNA synthesis. Priming of reverse transcription by these different enzymes does not require extensive annealing of the template to a oligonucleotide primer. The printer is the 3' end of a cleaved chromosomal site in the cases of the non-LTR retrotransposons and group II introns (Luan et al., "Reverse Transcription of R2Bm RNA is Primed by a Nick at the Chromosomal Target Site: A Mechanism for non-LTR Retrotransposition," *Cell* 72:595–605 (1993); and Cousineau et al., "Retrohoming of a Bacterial Group II Intron: Mobility Via Complete Reverse Splicing, Independent of Homologous DNA Recombination," *Cell* 94:451–462 (1998), each of which is hereby incorporated by reference in its entirety), the 3' end of the chromosome itself in the case of telomerase (Nakamura et al., "Telomerase Catalytic Subunit Homologs from Fission Yeast and Human," *Science* 277:955–959 (1997), which is hereby incorporated by reference in its entirety), the 2' hydroxyl of an internal G residue of the RNA template in the case of msDNA (Inouye and Inouye, "Bacterial Reverse Transcriptase," *In Reverse Transcriptase* (Goff, S. & Salka, A., eds). pp. 391–410, Cold Spring Harbor Press, Cold Spring Harbor, N.Y. (1993), which is hereby incorporated by reference in its entirety), and either de novo or the 3' end of another cDNA in the cases of the Mauriceville plasmid (Kennell et al., "The Mauriceville Plasmid of *Neurospora* spp. Uses Novel Mechanisms for Initiating Reverse Transcription in vitro," *Mol. Cell. Biol.* 14:3094–3107 (1994); and Wang and Lambowitz, "The Mauriceville Plasmid Reverse Transcriptase Can initiate cDNA Synthesis de novo and May Be Related to Reverse Transcriptase and DNA Polymerase Progenitor," *Cell* 75:1071–1081 (1993), each of which is hereby incorporated by reference in its entirety). Only retroviruses and LTR retrotransposons use an annealed RNA to prime reverse transcription of their RNA template (reviewed in Levin, "It's Prime Time for Reverse Transcriptase," *Cell* 88:5–8 (1997), which is hereby incorporated by reference in its entirety).

Another common feature of these various retroelement RTs is that the region of the protein homologous to the 'fingers' and 'palm' domains are considerably larger than that of the retroviruses (Xiong and Eickbush, "Origin and Evolution of Retroelements Based on their Reverse Transcriptase Sequences," *EMBO J.* 9:3351–3362 (1990), which is hereby incorporated by reference in its entirety). All non-viral reverse transcriptases contain an extra segment that is not found in retroviral RTs (Eickbush, "Origin and Evolutionary Relationships of Retroelements," *In The Evolutionary Biology of Viruses* (Morse, S. S. ed.), pp. 121–157, Raven Press, New York (1994), which is hereby incorporated by reference in its entirety), as well as additional segments in some groups. For example, non-LTR retrotransposons contain an additional segment between segment A and B, while group II intron RTs contain an extra region between segments B and C (Eickbush, "Origin and Evolutionary Relationships of Retroelements," *In The Evolutionary Biology of Viruses* (Morse, S. S. ed.), pp. 121–157, Raven Press, New York (1994); and Nakamura et al., "Telomerase Catalytic Subunit Homologs from Fission Yeast and Human," *Science* 277:955–959 (1997), each of which is hereby incorporated by reference in its entirety). Because the 'fingers' domain of retroviral RTs associates with the RNA template upstream of the active site (Kohlstaedt et al., "Crystal Structure at 3.5 Angstrom Resolution of HIV-1 Reverse Transcriptase Complexed with an Inhibitor," *Science* 256:1783–1790 (1992); and Sarafianos et al., "Crystal Structure of HIV-1 Reverse Transcriptase in Complex with a Polypurine Tract RNA:DNA," *EMBO J.* 20:1449–1461 (2001), each of which is hereby incorporated by reference in its entirety), these extra segments within the non-retroviral RTs are presumably involved in specific RNA-template interactions. Indeed, Chen and Lambowitz ("De novo and DNA Primer-mediated Initiation of cDNA Synthesis by the Mauriceville Retroplasmid Reverse Transcriptase Involve Recognition of a 3' CCA Sequence," *J. Mol. Biol.* 271:311–332 (1997), which is hereby incorporated by reference in its entirety) have suggested that this 'finger' domain is involved in specific recognition of the CCA sequence involved in de novo initiation of reverse transcription by the Mauriceville RT.

Figure 11A:
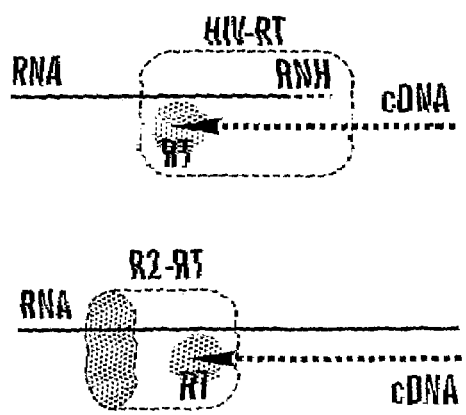
FIGS. 11A–C are schematic models which correlate the unusual abilities of the R2 RT to its structural differences from that of retroviral RT. Gray lines represent RNA; dotted lines represent cDNA; black lines represent DNA; and rounded rectangles represent protein. The active site of the RT is indicated by a diffuse shaded region.

In FIG. 11 above, a simple model for the R2 RT is provided which can help explain its different properties compared to retroviral enzymes. This model has many similarities to that proposed for the Mauriceville enzyme (Chen and Lambowitz, "De novo and DNA Primer-mediated Initiation of cDNA Synthesis by the Mauriceville Retroplasmid Reverse Transcriptase Involve Recognition of a 3' CCA Sequence," *J. Mol. Biol.* 271:311–332 (1997), which is hereby incorporated by reference in its entirety). Based on the additional amino acid motifs found in the palm and fingers regions of the R2 RT, and the demonstrated ability of the R2 enzyme to specifically bind its own RNA template, the R2 enzyme is shown to have significant binding potential to the RNA template upstream of the active site (FIG. 11A). There are two components to this template binding: specific affinity of the protein for the RNA structure assumed by the 3' UTR sequences of the R2 element, and the ability of the protein bind the free 3' end of any RNA molecule. The ability to bind RNA 3' ends could explain how the R2 protein can template jump onto a second RNA template when it completes transcription of the first RNA template (panel B). R2 RNA templates are preferred in these jumps because these RNAs have higher affinity for the RT. These properties of the R2 protein contrast with HIV RT and its associated RNase H domain in which the major interactions of the protein is with the RNA template downstream of the active site (Kohlstaedt et al., "Crystal Structure at 3.5 Angstrom Resolution of HIV-1 Reverse Transcriptase Complexed with an Inhibitor," *Science* 256:1783–1790 (1992); and Sarafianos et al., "Crystal Structure of HIV-1 Reverse Transcriptase in Complex with a Polypurine Tract RNA:DNA," *EMBO J.* 20:1449–1461 (2001), each of which is hereby incorporated by reference in its entirety). Template switching by retroviral enzymes involves annealing of the acceptor RNA to the cDNA downstream of the active site (Peliska and Benkovic, "Mechanism of DNA Strand Transfer Reactions Catalyzed by HIV-1 Reverse Transcriptase," *Science* 258: 1112–1118 (1992); and DeStefano et al., "Requirements for Strand Transfer Between Internal Regions of Heteropolymer Templates by Human Immunodeficiency Virus Reverse Transcriptase," *J. Virol.* 66: 6370–6378 (1992), each of which is hereby incorporated by reference in its entirety).

Figure 11B:
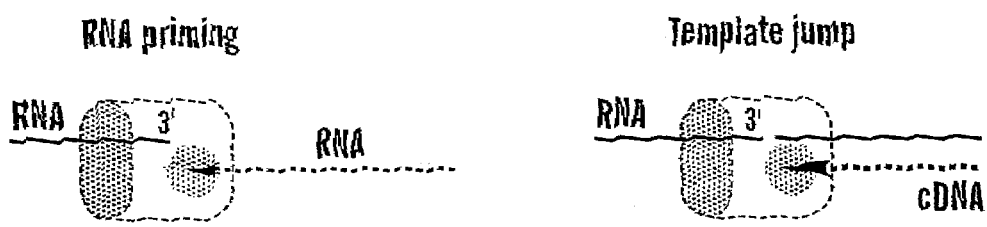
Figure 11C:
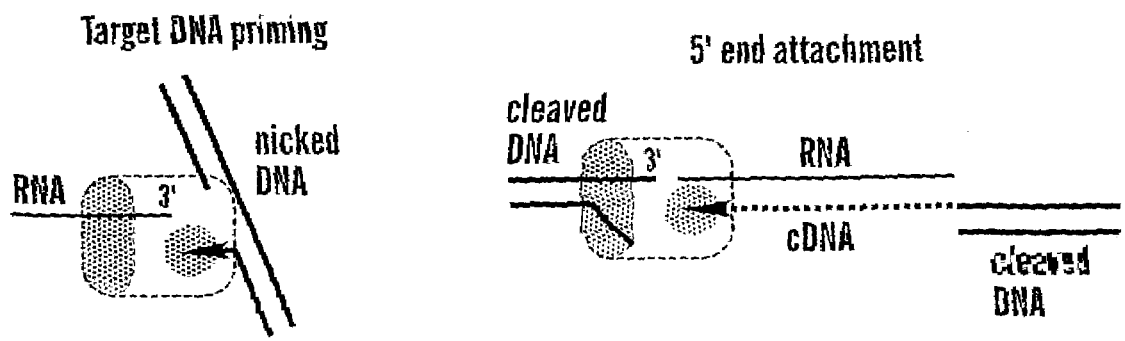

The absence of the RNase H domain in the R2 RT means that RNA 3' ends may also be able to bind the opposite (downstream) side of the RT active site (FIG. 11B). Thus, the ability of the R2 enzyme to use RNA to prime reverse transcription in the absence of sequence identity can be explained by the 3' ends of two RNA molecules simultaneously binding either end of the presumed major groove that contains the active site of the enzyme. The R2 RT has significant preference to use the R2 RNA as template (upstream binding), but little specificity for the RNA that primes the reaction (downstream binding).

Priming of reverse transcription by the DNA cleavage site can be viewed as similar to that of RNA-priming (panel C). When the R2 protein is bound to the nicked DNA target site, the 3' end of a cleaved DNA strand is positioned adjacent to the RT active site. When the R2 protein is free in solution, the 3' end of RNA can be bound to this site. In FIG. 11, the DNA end has been drawn unpaired (to be used as primer), to emphasize its potential similarity to the RNA-priming reaction; however, there is no direct evidence or this suggestion.

It seems unlikely that template jumping between RNA templates plays a role in R2 retrotransposition. However, the ability of the enzyme to conduct such jumps can be viewed as support for one possible model of how the 5' end of the reverse transcribed product is attached to the upstream DNA target site. Analysis of the sequence variation that exists at the 5' end of R2 elements from a number of arthropod species has led us to suggest a model in which the RT jumps from the R2 RNA template onto the upstream DNA target (FIG. 11C) (Burke et al., "The Domain Structure and Retrotransposition Mechanism of R2 Elements are Conserved Throughout Arthropods," *Mol. Biol. Evol.* 16:502–511 (1999); and George et al., "Analysis of the 5' Junctions of R2 Insertions with the 28S gene: Implications for non-LTR Retrotransposition," *Genetics* 142:853–863 (1996), each of which is hereby incorporated by reference in its entirety). R25' junction variation includes apparent non-templated nucleotides similar to those resulting from in vitro template jumps (FIGS. 2, 6 and 9). R25' junctions sometimes contain short deletions of the DNA upstream of the cleavage site. These deletions could be explained by the jumps occurring to internal nucleotides near the free 3' end, again as seen above during in vitro jumps (FIGS. 2, 6 and 9). Finally, many R25' junctions contain large deletions of the R2 element indicating that no sequences at the 5' end of the element are required for 5' attachment. These junctions are readily explained by template jumps occurring prematurely or from RNA templates that are not full-length.

Example 10

R2 RT is More Processive than Retroviral AMV RT

Figure 13:
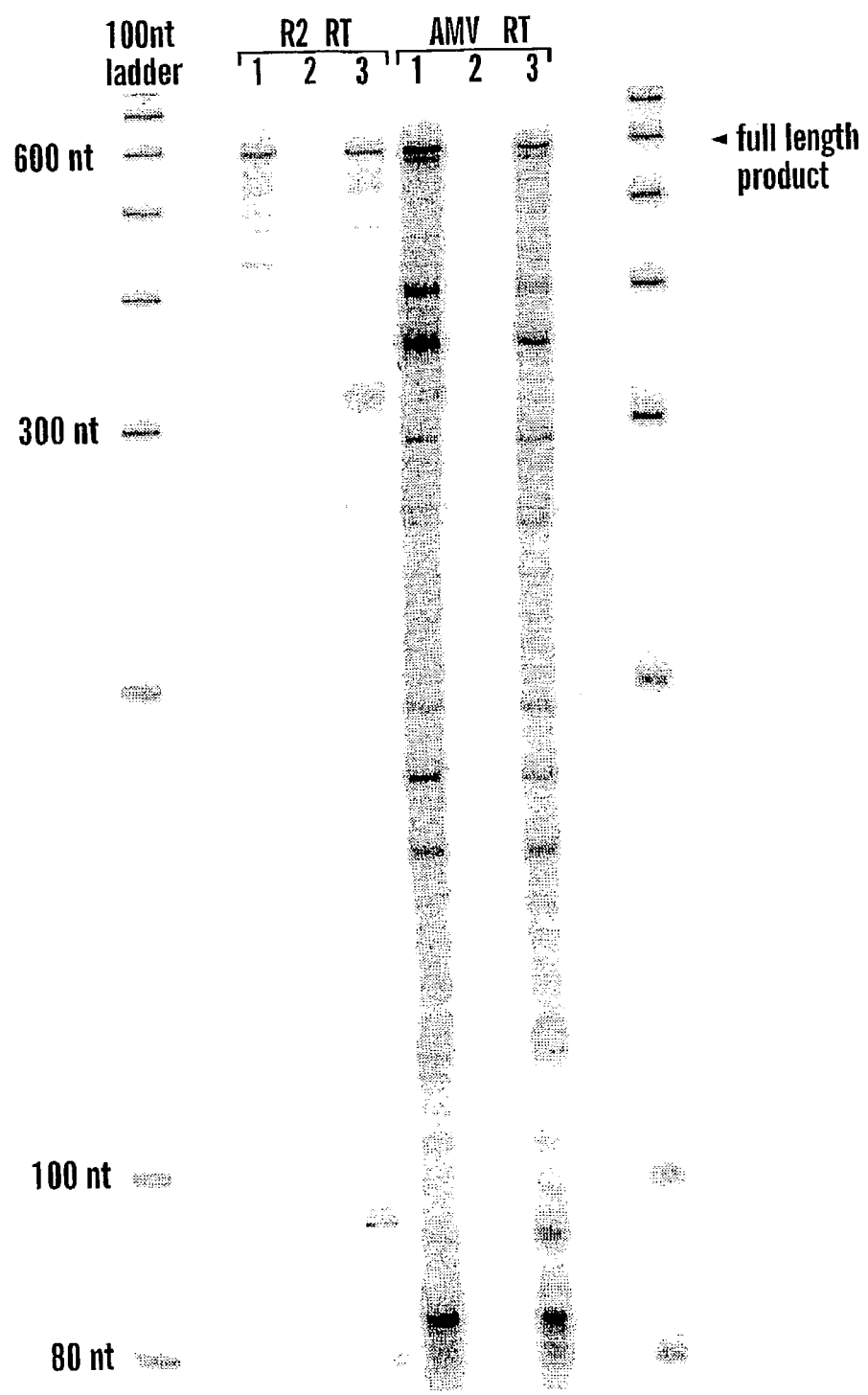
FIG. 13 is an autoradiograph which illustrates a processivity assay comparing R2 and AMV RTs on a 600 nt RNA template. 5' end-labeled AB.23 primer (SEQ ID No: 33, Table I) was annealed to the 600 nt vector RNA template as described above. Each lane contained 50 fmole of annealed RNA/DNA-primer. Reactions were started with the addition of 5 μl of 1.25 mM dNTP and then stopped after 5 min incubation in 37° C. In those reactions with R2 RT, 2 ng (20 pmole) of R2 RT was preincubated with the RNA/primer for 5 min at 37° C. in 50 mM Tris-HCl (pH 7.5), 0.2 M NaCl, 10 mM MgCl$_2$, 2.5 mM DTT, 0.01% Triton X-100 in final volume 25 μl. Lane 1, no other additions; lane 2, the preincubation mixture also contained 2.5 μl of "trap" (20 μg of heparin, ~1 μg of poly(rA)/poly(dT)13–18); lane 3, after preincubation the "trap" was added at the start of the reaction (addition of dNTP). In those reactions with AMV RT, 2.5 U of AMV RT (Promega) was preincubated with the RNA/primer for 5 min at 37° C. in 50 mM Tris-HCl (pH 8.3), 50 mM KCl, 5 mM MgCl$_2$, 5 mM DTT, 0.5 mM spermidine, in a final volume of 25 μl. Lane 1, no other additions; lane 2, the preincubation mixture also contained 2.5 μl of "trap" (20 μg of heparin, ~1 μg of poly(rA)/poly (dT) 13–18); lane 3, after preincubation the "trap" was added at the start of the reaction (addition of dNTP).

The length with which a polymerase can synthesize a nucleic acid before dissociating from its template is usually referred to as its processivity. High processivity is desired of any RT to make full-length cDNA copies of RNA. The retroviral AMV polymerase is one with the best characterized RTs and is known to be one of the most processive of the retroviral enzymes. FIG. 13 compares the processivity of the R2 RT with that of AMV RT in a simple primer extension assay with the 600 nt vector RNA as template. The reaction with AMV RT generates a larger percentage of cDNA products that are less than full length (AMW-RT, lane 1) compared to the R2 protein (R2-RT, lane 1). To confirm that the reaction products seen in FIG. 13 reflect the processivity of each enzyme (i.e., the length of cDNA synthesized before the RT dissociates from the RNA template) and not multiple rounds of elongation, the reactions were also conducted under conditions that do not allow the reinitiation of RT after its dissociation. These single round reactions, also called RT trap assays, involve the addition of heparin and an excess of poly(A)/oligoT. Heparin inhibits reinitiation while any reinitiation that might occur will be predominately onto the more abundant poly(A)/oligo dT templates. To demonstrate the efficiency of the 'trap', lane 2 for each enzyme represents the addition of heparin and the poly(A)/oligo dT at the same time as the addition of the RT, thus preventing any synthesis of cDNA primed by the end-labeled DNA primer annealed to the 600 nt RNA.

Figure 14A:
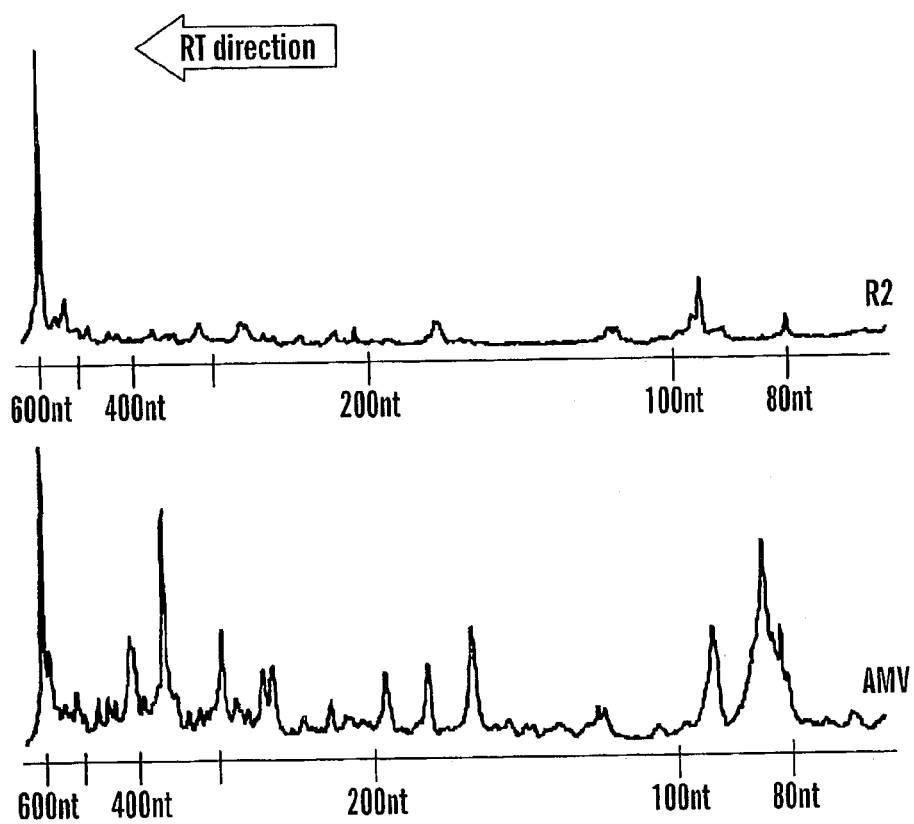
FIGS. 14A–B are scans of the RNA processivity assay using a 600 nt (14A) and 1094 nt (14B) RNA templates.

In lane 3 of each panel, the RTs are first bound to the DNA primer/RNA template complex and then heparin and poly (A)/oligo dT are added along with dNTPs to start reverse transcription. The length distribution of the cDNA synthesized by AMV RT in the presence of the trap was again significantly shorter than cDNA synthesized by the R2-RT. The difference in the accumulation of cDNA transcripts by the R2 and AMV RTs are also illustrated by the graph in FIG. 14A. The tracings in this Figure represent the RT product found in lane 3 of each enzyme in FIG. 13. The yield of full-length cDNA product (600 nt) versus total cDNA (all bands between 100–600 nt) was determined. The level of full-length products with R2 was ~16% of the total synthesis or nearly four times higher than with AMV-RT (4.1%).

Figure 14B:
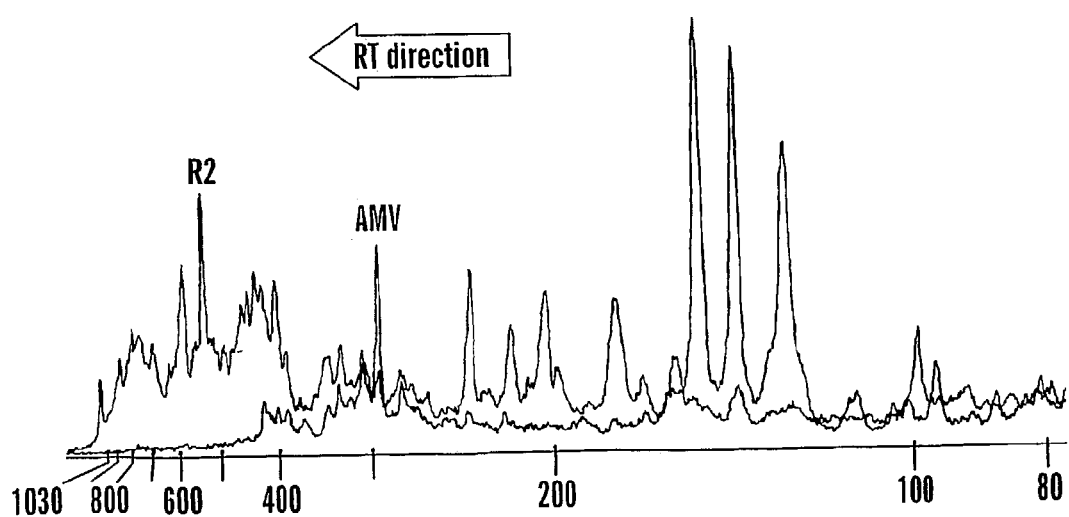

Similar processivity comparisons between the R2 and AMV RTs were also conducted with the 1094 nt RNA derivative of the pBSKII(SK–) plasmid (FIG. 14B). Reverse transcription of the 1094 nt template by AMV-RT yields essentially no cDNA products longer than 450 nt. In contrast the R2 RT yields considerable cDNA products over 500 nt in length with a distinct full-length band at 1094 nt These observations clearly suggest that under the conditions of these single round elongation reactions, R2 RT is more processive than the AMV-RT. It should be mentioned that the cDNA distribution in the non-trap and trap reactions in FIG. 13 (lanes 1 and 3 respectively) are similar for both enzymes. This result can be explained by the very short reaction times and low polymerase concentrations used in these assays. Both conditions significantly decrease the probability of reinitiation of the RT after it has dissociated.

Finally, it should be noted that the cDNA that are less than full-length differed dramatically for the R2 and AMV RTs.

In the case of the 600 nt template, the RT products generated by AMV reveals several distinct bands that are distributed along the RNA, while the distribution of RT products generated by the R2-RT are more diffuse with only one distinct band of ~95 nt. In the case of the 1096 nt RNA, AMV produced distinct bands of lengths 130, 145, 160 and 300 nt, while the R2-RT produced weaker, but still distinct bands of lengths 100, 180, 200, 220 and 240 nt. These differences in the length of the truncated cDNA reflect the different abilities of the RTs to transcribe regions of RNA with different primary and secondary structure. They also indicate that the shorter cDNA products produced by the RT are a result of enzyme dissociation and not the result of a degraded RNA template.

Example 11

Figure 15A:
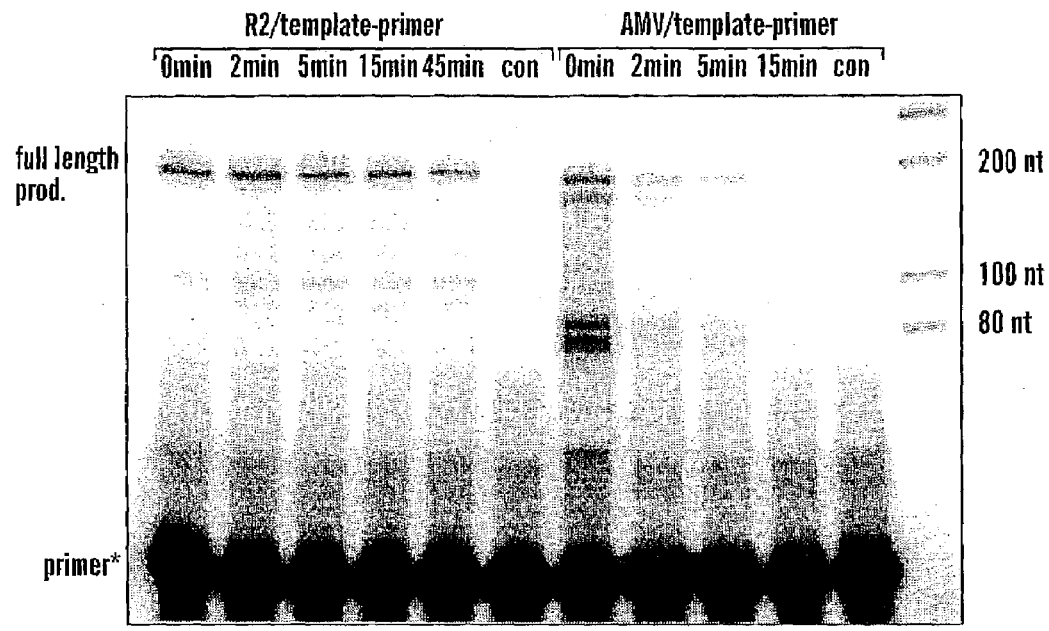
FIGS. 15A–B illustrate the dissociation rates of R2 RT and AMV RT from an RNA template.
Figure 15B:
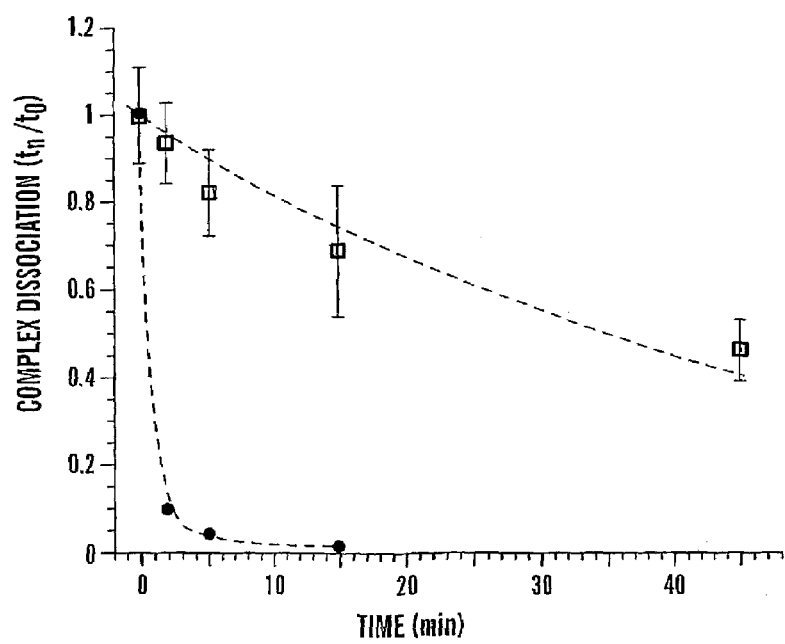

The Higher Processivity of R2 is a Result of its Reduced Rate of Dissociation from the RNA Template The higher processivity of the R2 RT compared to retroviral RTs could be a result of two properties. First, it might dissociate from the RNA template at a slower rate than retroviral enzymes. Second, it might elongate cDNA at a faster rate than the retroviral enzymes. To compare the dissociation rates of R2 and AMV RT, the 183 nt vector RNA with annealed end-labeled DNA primer was first preincubated with the appropriate RT to allow protein binding. To this complex were added heparin and excess poly (A)/oligo dT (the trap). After various periods of time, dNTPs are added to initiate reverse transcription, and the products are separated on polyacrylamide gels (FIG. 15A). The total amount of cDNA synthesis at each time point was determined on a phosphoimager and plotted in FIG. 15B. This experiment demonstrated a dramatic difference in the dissociation rate of the two RTs. The level of cDNA products generated by the R2-RT decreased only 2 fold even after a 45 minute incubation. Meanwhile the level of cDNA products generated by the AMV-RT decreased 10-fold after only a 2 minute pre-incubation with the trap.

The data was fit using decreasing single exponential function $\exp(-k_{off}*x)$ and the dissociation rate was determined ($k_{off}=0.33\pm0.04\times10^{-3}$ $sec^{-1}$). Because it can be argued that absence of substrate dNTP may significantly change the properties of the protein/template complex and, thus, may affect its stability, another stability experiment was conduct similar to that in FIG. 15A, but containing 5 µM dATP in the preincubation mixture. This nucleotide is the first to be incorporated from this RNA template and, thus, should represent complexes that have initiated reverse transcription. The $k_{off}$ determined under these conditions was not significantly different ($k_{off}=0.27\times10^{-3}$ $sec^{-1}$). The approximate $k_{off}$ determined for the AMV protein in the experiment in FIG. 15 ($k_{off}=0.019\pm0.0021$ $sec^{-1}$) is in good agreement with published values for the half time of AMV RT binding (~30s), e.g., by DeStefano et al., *J. Biol. Chem.* 266: 7423–7431 (1991), which is hereby incorporated by reference in its entirety.

Thus, the R2-RT dissociates from an RNA template nearly 60-fold slower than AMV-RT.

Figure 16A:
FIGS. 16A–B illustrate the elongation rate of R2 RT.
Figure 16B:
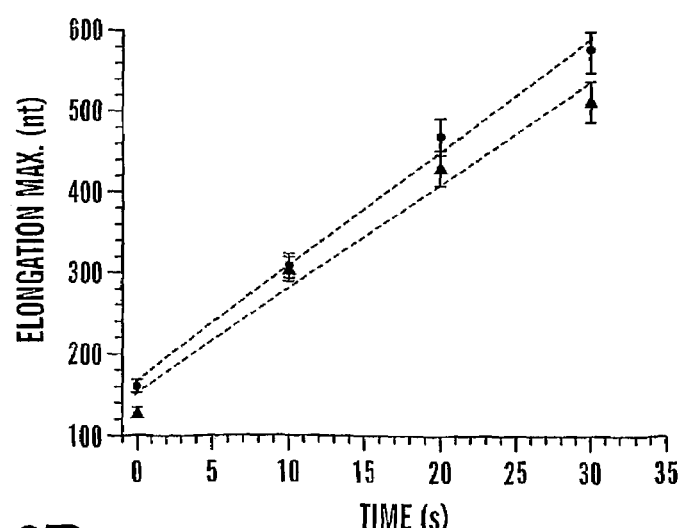

To determine the elongation rates of the R2 RT, the protein was preincubated with the 1090 nt vector RNA/end-labeled DNA primer complex to allow association. The four-dNTPs were then added for short periods of time and the reaction abruptly stopped by the addition of SDS and ethanol. The cDNA products from the R2 RT are shown in FIG. 16A. The maximum length of cDNA synthesized at each time point can be used to determine an elongation rate of 11.0 nt/sec. This reaction has been conducted with a number of different templates. Plotted in FIG. 16B is a similar experiment conducted with a 600 nt RNA template using both R2 and AMV RT. In this experiment, the R2 RT elongation rate was calculated to be 14.7 nt/sec similar to the rate calculated for the AMV-RT (12.9 nt/sec).

The combined results of FIGS. 15 and 16 demonstrate that the increased processivity of the R2 protein is a result of it higher stability on (i.e. reduced rate of dissociation from) the RNA template.

Example 12

The R2 RT is not Blocked by the Secondary Structure of the RNA Template

Figure 17A:
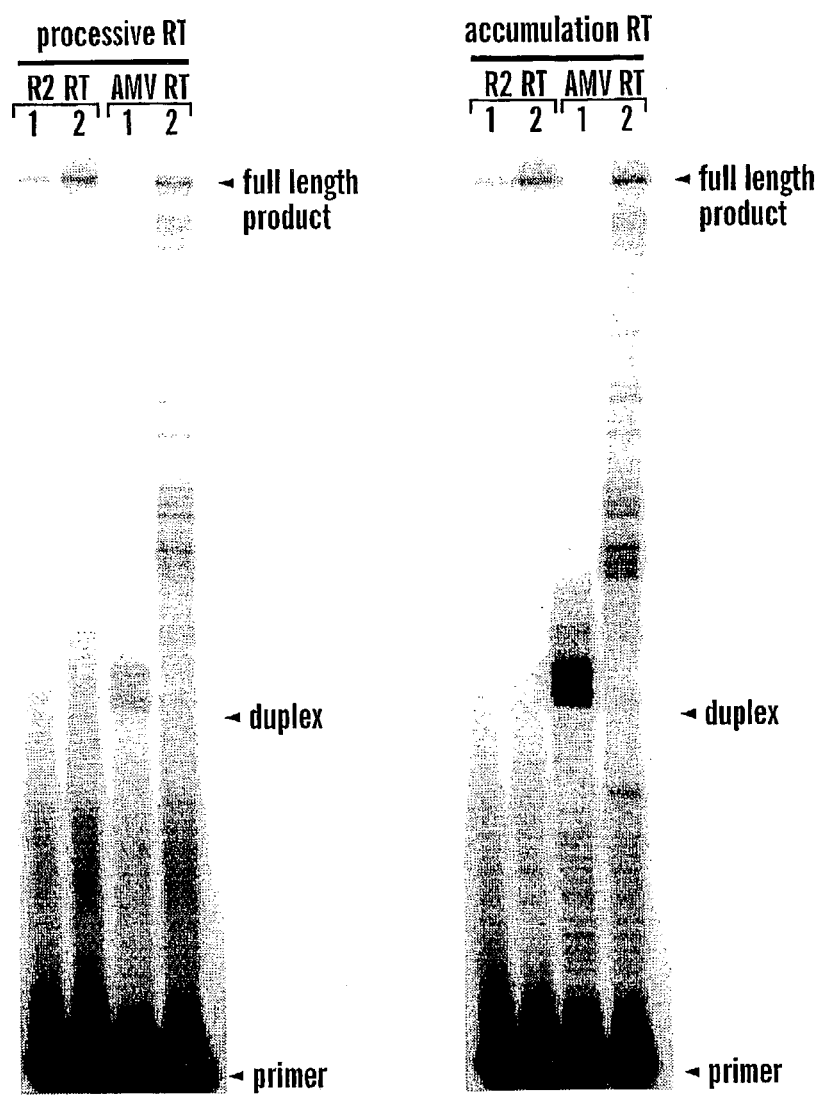
FIG. 17A is an autoradiograph which illustrates how R2 RT is unaffected by RNA secondary structure. The RNA template for this reaction has an annealed primer near the middle of the RNA and a longer RNA block annealed to the 5' end of the RNA (FIG. 17B). This template was formed by the annealing of 300 ng (3 pmole) of 334 nt RNA, 25 ng (4 pmole) of end-labeled DNA primer AB.8 (SEQ ID No: 27, Table I), and 300 ng (8 pmol) of 117 nt RNA. The DNA template for the production of the 117 nt RNA was pBSK (SK−) digested with KpnI. RNA was synthesized with T3 RNA polymerase. The procedure of annealing was similar to that of all other annealing reaction described above. The 334 nt RNA template without the RNA block was prepared in a similar manner. For each primer extension reaction, about 300 fmole of annealed template preincubated with either 2 ng (20 fmole) of R2 or 1.5 U of AMV RT (Promega). Preincubations with enzymes were for 5 min. at 37° C. After preincubation, reverse transcription was started by addition 5 μl of 1.25 mM dNTP, and stopped after 5 min at 37° C. In the processive runs (left panel) 2.5 μl of "trap"(20 μg of heparin, 1 μg of poly(A)/poly(dT)13–18) was added along with 2.5 μl of 2.5 mM dNTP to start the reaction.
Figure 17B:
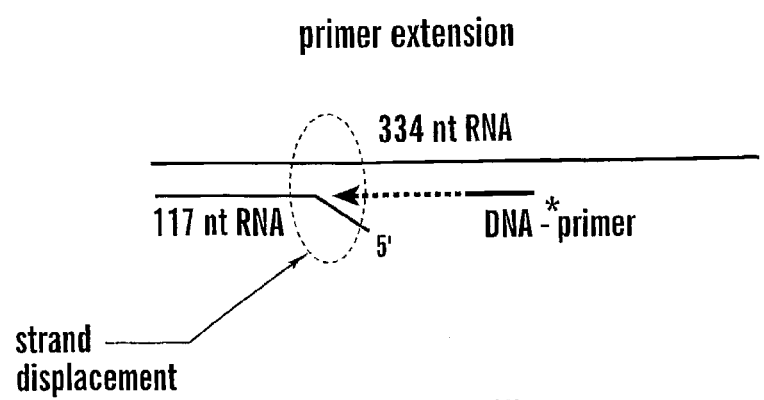

The presence of truncated cDNA bands that are of specific-lengths (see FIGS. 13–15), rather than a continuous range of cDNA lengths expected from a gradual dissociation of the RT from the RNA template, is believed to be a result of the RT pausing at structural features of the RNA template. As was suggested in the discussion to the data in FIGS. 13 and 14, it appears that the R2 RT responds differently and not as severely to these structural features, because the yield and sizes of these truncated cDNAs differed for the two enzymes. To directly determine the effects of RNA structure of the ability of the R2 protein to reverse transcribe RNA templates, RNA templates were engineered to contain precise hair-pin loops. It was determined that the R2 protein was readily able to transcribe through these loops. Unfortunately, DNA sequences with extremely long such loops that can be transcribed by T7 RNA polymerase are difficult to clone in on bacterial plasmids. Therefore, a somewhat different approach was utilized to generate such stable hairpins by simply annealing two complimentary RNA molecules. The experimental approach (diagramed in FIG. 17B) involved the 334 nt RNA template to which is annealed both a 19 nt oligodeoxynucleotide near the middle of the RNA (the primer), and a 117 nt RNA that is a perfect complement to the 5' end of the RNA (the block). cDNA synthesis is monitored on gels by means of the end-labeled DNA primer. Both the R2 and AMV enzymes were tested with and without the RNA block (lanes 1 and 2, respectively) under two conditions: the presence of the poly(A)/oligo dT trap (left panel) and the absence of a trap to allow multiple re-initiations (right panel).

With the R2 RT, only full-length cDNA products are generated irrespective of whether the RNA template contains the RNA block (lane 1) or in the absence of the RNA block (lane 2). In the case of the AMV-RT the presence of the RNA block completely prevents any cDNA synthesis more than a few nucleotides past the beginning of the block. In the absence of the RNA block, full length products are obtained with the AMV-RT, but even here much of the cDNA stops near the middle of the RNA, presumably as a result of a the RNA secondary structure. These results dramatically reveal that the R2 RT is not significantly blocked by duplex regions of RNA templates. In another set of experiment, the R2 protein was determined to be capable of readily reverse transcribing poly(A) templates that are saturated by oligo(dT). Under these same conditions where AMV-RT is severely inhibited.

At this point it is not clear whether the ability of the R2 RT to reverse transcribe through the annealed RNA is a result of the protein's ability to actively displace the annealed RNA strand from the template, or whether the remarkable stability of the R2 protein on its RNA template allows the enzyme to passively move through the duplex region during the random opening and closing (sometimes called breathing) associated with the ends of duplex nucleic acids.

Example 13

Effects of Temperature on the Reverse Transcription Reactions

Figure 18:
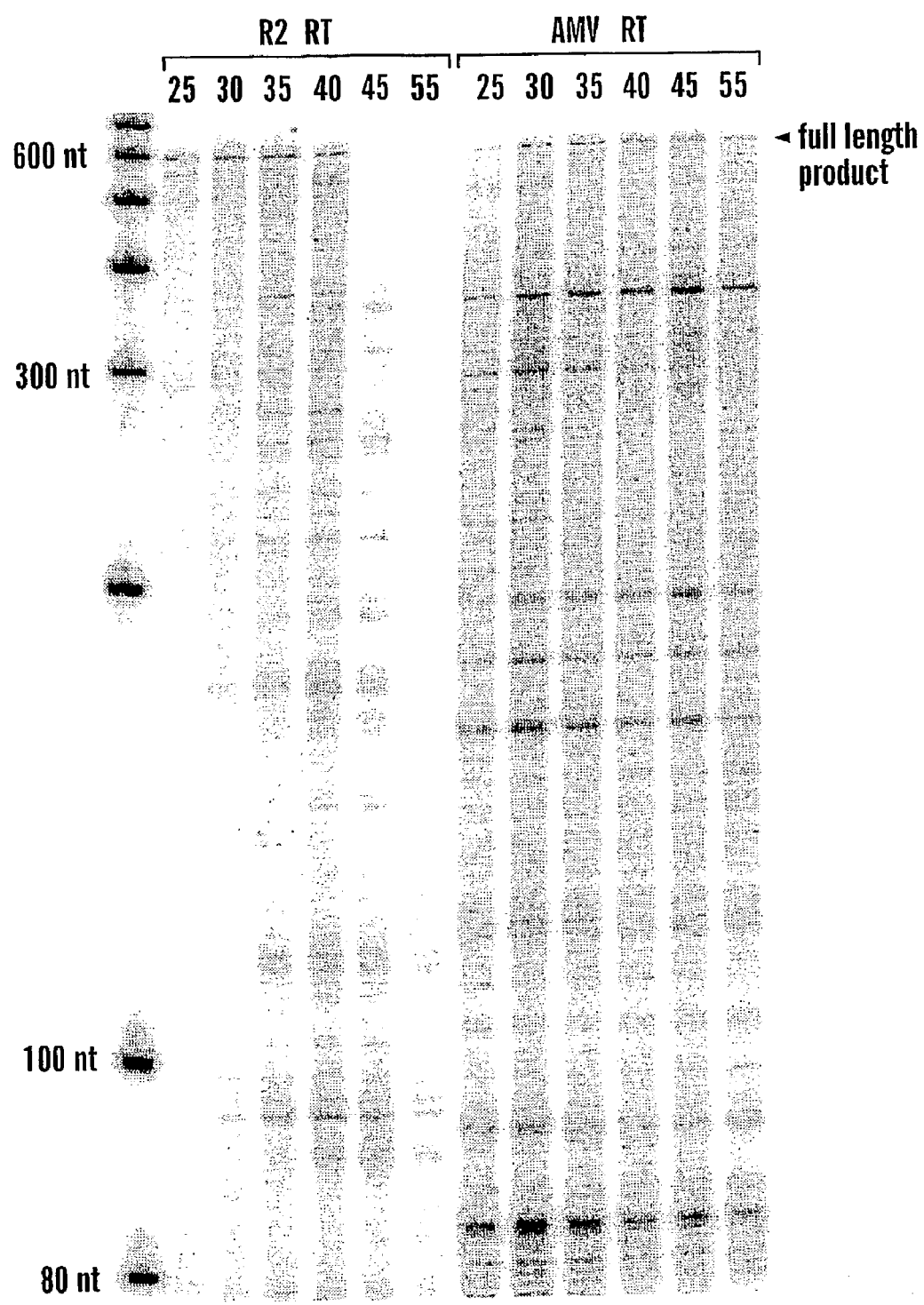
FIG. 18 is an autoradiograph which illustrates the effects of temperature on RT processivity. The template and reaction condition are exactly like those described with respect to FIG. 13 for a processive run (i.e., with the trap), except that preincubation was for 20 min at 25° C. followed by a short (2 min) equilibration at the new temperature (25° C.–55° C. in 5° C. increments). The elongation reaction was started by the addition of dNTPs and the trap and were conducted for 5 minutes
Figure 19:
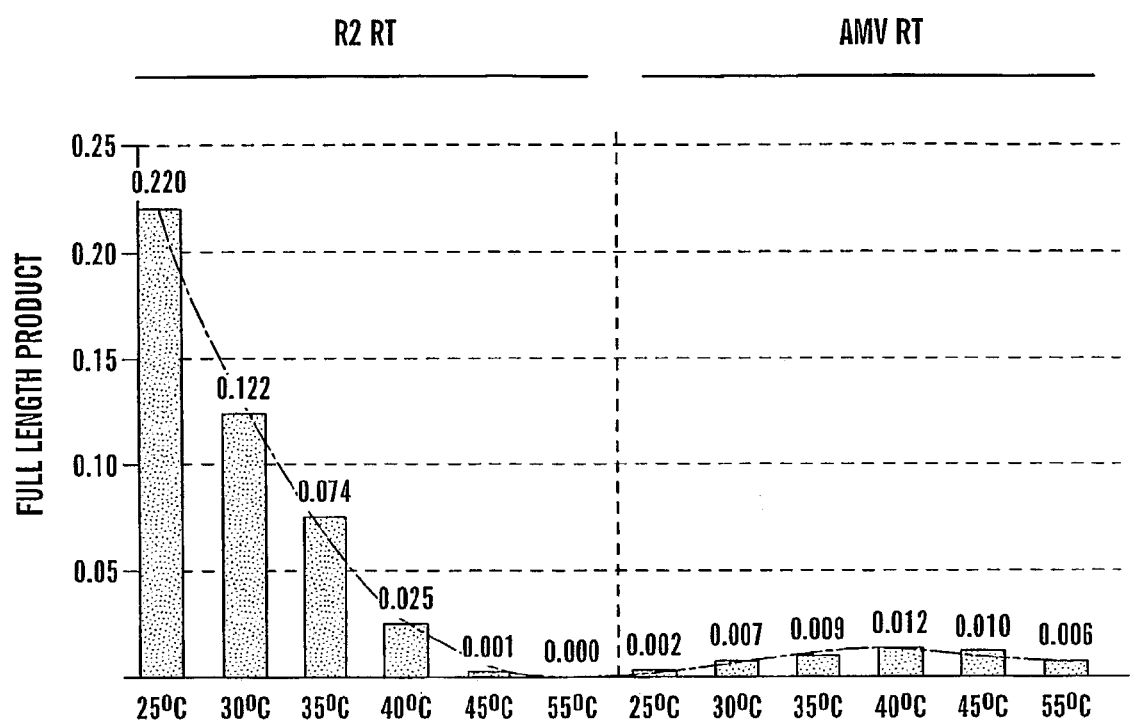
FIG. 19 is a graph which illustrates the percentage of the cDNA products that are full-length (600 nt) as a function of temperature. The graph is an analysis of the data in FIG. 18. Plotted is the fraction of the total cDNA (all cDNA between 100 and 600 nt in FIG. 18) that corresponds to full length (600 nt). The left panel is for R2 RT and the right panel is for AMV RT.

Because weak RNA secondary structures are known to be highly dependent upon the temperature of the solution, increasing the temperature of the reaction is sometimes used as a means to minimize the effects of RNA structure on a RT reaction. In FIG. 18, the ability of the R2 and AMV RTs to reverse transcribe the 600 nt RNA template at temperatures ranging from 25° C. to 55° C. are compared. The reactions were again conducted for short periods with low concentration of RT to promote the formation of products derived from only a single round of enzyme association. The total cDNA produced at each temperature was determined on a phosphoimager, and the fraction of the cDNA corresponding to full-length cDNA (~600 nt) at each temperature is plotted in FIG. 19.

In the case of the AMV-RT high levels of cDNA synthesis was obtained at all temperatures, but the percentage of the cDNA product corresponding to full-length transcripts never exceeded 1.2%. The nature of the truncated products did not substantially differ at the different temperatures suggesting that the changes in the secondary structure of the RNA associated with these different temperatures had minimal effect of enzyme dissociation.

In the case of the R2 RT, the total amount of cDNA synthesis increased from 25° C. to 40° C. at which point further temperature increases caused a dramatic loss of activity. This loss of activity is presumably as a result of the denaturation of the protein. Surprisingly, even though the R2 protein is less active at lower temperatures, the fraction of the total cDNA that was full-length increased, such that at 25° C. over 20% of that cDNA is full-length. These results could be explained if rising temperatures increase the dissociation rate of the R2 protein from the RNA template to a greater extend than they increase the elongation rate.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of preparing a cDNA molecule comprising:
contacting an RNA molecule, in the presence of dNTPs, with a non-LTR retrotransposon protein or polypeptide having reverse transcriptase activity, wherein the non-LTR retrotransposon protein or polypeptide is an R2 protein or polypeptide, under conditions effective for production of a cDNA molecule complementary to the RNA molecule, said contacting being carried out in the absence of a target DNA molecule of the non-LTR retrotransposon protein or polypeptide; and
isolating the cDNA molecule.

2. The method according to claim 1, wherein the R2 protein or polypeptide is derived from an arthropod.

3. The method according to claim 1, wherein the RNA molecule lacks a primer site to initiate reverse transcription.

4. The method according to claim 1, wherein the RNA molecule lacks a polyadenylation region.

5. The method according to claim 1, wherein said contacting is carried out in the presence of both a donor RNA molecule having a known sequence and an acceptor RNA molecule having a known sequence.

6. The method according to claim 1, wherein said contacting is carried out in the presence of a donor RNA molecule having a known sequence.

7. The method according to claim 1, wherein said contacting is carried out in the presence of an acceptor RNA molecule having a known sequence.

8. The method according to claim 1, wherein said contacting is carried out under isothermic conditions.

9. The method according to claim 1, wherein said contacting is carried out at a temperature of between about 20° C. and about 40° C.

10. The method according to claim 1, wherein the RNA molecule includes a structure or an annealed duplex region that would interfere with retroviral reverse transcriptase function.

11. The method according to claim 1, wherein said contacting is carried out under conditions whereby a significant portion of the isolated cDNA molecules are substantially full length reverse transcripts of the RNA molecule.

12. The method according to claim 1, wherein the RNA molecule includes a polyadenylated region, the method further comprising:
annealing a primer to the polyadenylated region of the RNA molecule prior to said contacting.

13. A method of amplifying a cDNA molecule comprising:
performing the method of claim 1 to obtain a single-stranded cDNA molecule that includes a region of interest;
annealing a first primer to the single-stranded cDNA molecule at a position 3' of the region of interest; and
extending the first primer to form a complementary DNA strand including a complement of the region of interest.

14. The method according to claim 2, wherein the arthropod is *Bombyx mori*.

15. A method of amplifying a cDNA molecule comprising:
performing the method according to claim 5 to obtain a single-stranded cDNA molecule that includes a region of interest, a region complementary to the donor RNA 5' of the region of interest, and a region complementary to the acceptor RNA 3' of the region of interest;

annealing a first primer to the single-stranded cDNA molecule at a position 3' of the region of interest; and
extending the first primer to form a complementary DNA strand including a complement of the region of interest.

16. The method according to claim 9, wherein said contacting is carried out at a temperature of between about 21° C. and about 35° C.

17. The method according to claim 12, wherein said contacting is carried out in the presence of an acceptor RNA molecule having a known nucleotide sequence.

18. A method of amplifying a cDNA molecule comprising:
performing the method according to claim 17 to obtain a single-stranded cDNA molecule that includes a region of interest, an oligoT region 5' of the region of interest, and a region complementary to the acceptor RNA 3' of the region of interest;
annealing a first primer to the single-stranded cDNA molecule at a position 3' of the region of interest; and
extending the first primer to form a complementary DNA strand including a complement of the region of interest.

19. The method according to claim 13 further comprising:
dissociating the complementary DNA strand from the single-stranded cDNA molecule;
annealing a second primer to the complementary DNA strand molecule at a position 3' of the complement of the region of interest; and
extending the second primer to form a second complementary DNA strand which is substantially the same as the single-stranded cDNA molecule at the region of interest.

20. The method according to claim 13, wherein said performing is carried out under conditions effective for the non-LTR retrotransposon protein or polypeptide to jump from the RNA molecule to an acceptor RNA molecule having a known sequence, the single-stranded cDNA molecule comprising a first portion complementary to the RNA molecule and a second portion complementary to the acceptor RNA molecule, the second portion being located 3' of the first portion.

21. The method according to claim 13, wherein said performing is carried out under conditions effective for the non-LTR retrotransposon protein or polypeptide to jump from a donor RNA molecule having a known sequence to the RNA molecule, the single-stranded cDNA molecule comprising a first portion complementary to the donor RNA molecule and a second portion complementary to the RNA molecule, the second portion being located 3' of the first portion.

22. The method according to claim 13 further comprising:
exposing the single-stranded cDNA molecule to a terminal transferase in the presence of dCTPs to form an oligoC tail at the 3' end of the single-stranded cDNA molecule.

23. The method according to claim 13, wherein said performing is carried out under isothermic conditions.

24. The method according to claim 13, wherein said performing is carried out at a temperature of between about 20° C. and about 40° C.

25. The method according to claim 13, wherein said performing is carried out at a temperature of between about 21° C. and about 35° C.

26. The method according to claim 19 further comprising:
dissociating the second complementary DNA strand from the complementary DNA strand; and
repeating said annealing and extending of the first and second primers, using the second complementary DNA strand, to form third and fourth complementary DNA strands, the third complementary DNA strand being substantially the same as the first complementary strand and the fourth complementary DNA strand being substantially the same as the second complementary strand.

27. The method according to claim 20, wherein the primer anneals to the second portion of the single-stranded cDNA molecule.

28. The method according to claim 22, wherein said exposing is carried out prior to said annealing the first primer and the first primer anneals to the oligoC tail.

29. The method according to claim 15 further comprising:
dissociating the complementary DNA strand from the single-stranded cDNA molecule;
annealing a second primer to the complementary DNA strand molecule at a position 3' of the complement of the region of interest; and
extending the second primer to form a second complementary DNA strand which is substantially the same as the single-stranded cDNA molecule at the region of interest.

30. The method according to claim 29 further comprising:
dissociating the second complementary DNA strand from the complementary DNA strand; and
repeating said annealing and extending of the first and second primers, using the second complementary DNA strand, to form third and fourth complementary DNA strands, the third complementary DNA strand being substantially the same as the first complementary strand and the fourth complementary DNA strand being substantially the same as the second complementary strand.

31. The method according to claim 18 further comprising:
dissociating the complementary DNA strand from the single-stranded cDNA molecule;
annealing a second primer to the complementary DNA strand molecule at a position 3' of the complement of the region of interest; and
extending the second primer to form a second complementary DNA strand which is substantially the same as the single-stranded cDNA molecule at the region of interest.

32. The method according to claim 31 further comprising:
dissociating the second complementary DNA strand from the complementary DNA strand; and
repeating said annealing and extending of the first and second primers, using the second complementary DNA strand, to form third and fourth complementary DNA strands, the third complementary DNA strand being substantially the same as the first complementary strand and the fourth complementary DNA strand being substantially the same as the second complementary strand.

* * * * *

SEQUENCE LISTING

```
<160> NUMBER OF SEQ ID NOS: 38

<210> SEQ ID NO 1
<211> LENGTH: 24
<212> TYPE: RNA
<213> ORGANISM: Artificial Sequence
<220> FEATURE:
<223> OTHER INFORMATION: Description of Artificial Sequence:  3'
      terminal sequence of 274 base R2 RNA

<400> SEQUENCE: 1
uuuuaucggu uuacggagca guag                                              24

<210> SEQ ID NO 2
<211> LENGTH: 10
<212> TYPE: RNA
<213> ORGANISM: Artificial Sequence
<220> FEATURE:
<223> OTHER INFORMATION: Description of Artificial Sequence:  5'
      terminal sequence of 274 base R2 RNA

<400> SEQUENCE: 2
ccaacucgga                                                              10

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:  reverse
      transcription product

<400> SEQUENCE: 3
tttatcggtt tacggagcag tagccaactc gga                                    33

<210> SEQ ID NO 4
<211> LENGTH: 34
```

<212> TYPE: DNA
<213> ORGANISM: Artificial Sequence
<220> FEATURE:
<223> OTHER INFORMATION: Description of Artificial Sequence: reverse
      transcription product

<400> SEQUENCE: 4
tttatcggtt tacggagcag tagaccaact cgga                    34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 5
tttatcggtt tacggagcag tagcccaact cgga                    34

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 6
tttatcggtt tacgtagccc aactcgga                           28

<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: 3' end of
      254 base R2 RNA

<400> SEQUENCE: 7
uccggcgcga ugaaaa                                        16

<210> SEQ ID NO 8
<211> LENGTH: 17
<212> TYPE: RNA
<213> ORGANISM: Artificial Sequence
<220> FEATURE:
<223> OTHER INFORMATION: Description of Artificial Sequence: 5' end of
      334 base R2 RNA

<400> SEQUENCE: 8
cccgcuuaac ccauggc                                       17

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 9
tccggcgcga tgaaaaaccc gcttaacccca tggc                   34

<210> SEQ ID NO 10
<211> LENGTH: 33
<212> TYPE: DNA

<213> ORGANISM: Artificial Sequence
<220> FEATURE:
<223> OTHER INFORMATION: Description of Artificial Sequence: reverse
      transcription product

<400> SEQUENCE: 10
tccggcgcga tgaaaacccg cttaacccat ggc                          33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 11
tccggcgcga tgaaagccg cttaacccat ggc                           33

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 12
tccggcgcgg gcatggc                                            17

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 13
tccggcgcga tgaaaacgcc ccccctcga                               29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 14
tccggcgcga tgaaaattc cctttagt                                 28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: reverse
      transcription product

<400> SEQUENCE: 15
tccggcgcga tttttgcttt tcttcc                                  26

<210> SEQ ID NO 16
<211> LENGTH: 17
<212> TYPE: DNA
<213> ORGANISM: Artificial Sequence

```
-continued

<220> FEATURE:
<223> OTHER INFORMATION: Description of Artificial Sequence:  3' end of
      54 base ssDNA template

<400> SEQUENCE: 16
aactatgact ctcttaa                                                         17

<210> SEQ ID NO 17
<211> LENGTH: 15
<212> TYPE: RNA
<213> ORGANISM: Artificial Sequence
<220> FEATURE:
<223> OTHER INFORMATION: Description of Artificial Sequence:  5' end of
      254 base R2 RNA

<400> SEQUENCE: 17
gguugagccu ugcac                                                           15

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:  reverse
      transcription product

<400> SEQUENCE: 18
aactatgact ctcttaaggt tgagccttgc ac                                        32

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:  reverse
      transcription product

<400> SEQUENCE: 19
aactatgact ctcttaaacg ttgagccttg cac                                       33

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:  reverse
      transcription product

<400> SEQUENCE: 20
aactatgact ctcttttttg agccttgcac                                           30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:  reverse
      transcription product

<400> SEQUENCE: 21
aactatgatg gttgagcctt gcac                                                 24

<210> SEQ ID NO 22
<211> LENGTH: 1114
<212> TYPE: PRT
<213> ORGANISM: Bombyx mori R2 element
```

<400> SEQUENCE: 22

```
Met Met Ala Ser Thr Ala Leu Ser Leu Met Gly Arg Cys Asn Pro Asp
 1               5                  10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Ala Glu Glu Ala Gly
225                 230                 235                 240

Glu Glu Arg Cys Ala Glu Asp Ala Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
        355                 360                 365

Leu His Ala Leu Gly Arg Ala Glu Trp His Gly Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415
```

-continued

```
Trp Arg Ala Val Pro Val His Leu Lys Ala Glu Met Phe Asn Ala Trp
        420                 425                 430
Met Ala Arg Gly Glu Ile Pro Glu Ile Leu Arg Gln Cys Arg Thr Val
        435                 440                 445
Phe Val Pro Lys Val Glu Arg Pro Gly Gly Pro Gly Glu Tyr Arg Pro
        450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                485                 490                 495
Ile Cys Ala Asp Gly Thr Leu Glu Asn Ser Ala Val Leu Asp Ala Val
                500                 505                 510
Leu Gly Asp Ser Arg Lys Lys Leu Arg Glu Cys His Val Ala Val Leu
                515                 520                 525
Asp Phe Ala Lys Ala Phe Asp Thr Val Ser His Glu Ala Leu Val Glu
                530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
                580                 585                 590
Ser Pro Ile Leu Phe Asn Val Val Met Asp Leu Ile Leu Ala Ser Leu
                595                 600                 605
Pro Glu Arg Val Gly Tyr Arg Leu Glu Met Glu Leu Val Ser Ala Leu
        610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
                660                 665                 670
His Arg Lys Lys His His Tyr Leu Thr Glu Arg Thr Phe Asn Ile Gly
        675                 680                 685
Gly Lys Pro Leu Arg Gln Val Ser Cys Val Glu Arg Trp Arg Tyr Leu
        690                 695                 700
Gly Val Asp Phe Glu Ala Ser Gly Cys Val Thr Leu Glu His Ser Ile
705                 710                 715                 720
Ser Ser Ala Leu Asn Asn Ile Ser Arg Ala Pro Leu Lys Pro Gln Gln
                725                 730                 735
Arg Leu Glu Ile Leu Arg Ala His Leu Ile Pro Arg Phe Gln His Gly
        740                 745                 750
Phe Val Leu Gly Asn Ile Ser Asp Asp Arg Leu Arg Met Leu Asp Val
        755                 760                 765
Gln Ile Arg Lys Ala Val Gly Gln Trp Leu Arg Leu Pro Ala Asp Val
770                 775                 780
Pro Lys Ala Tyr Tyr His Ala Ala Val Gln Asp Gly Gly Leu Ala Ile
785                 790                 795                 800
Pro Ser Val Arg Ala Thr Ile Pro Asp Leu Ile Val Arg Arg Phe Gly
                805                 810                 815
Gly Leu Asp Ser Ser Pro Trp Ser Val Ala Arg Ala Ala Ala Lys Ser
                820                 825                 830
```

```
Asp Lys Ile Arg Lys Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
    850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
    930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
        995                 1000                1005

Asp Val Gln Val Val Ser Gly Gln Arg Ser Leu Asp Glu Leu His Arg
    1010                1015                1020

Glu Lys Arg Asn Lys Tyr Gly Asn His Gly Glu Leu Val Glu Leu Val
1025                1030                1035                1040

Ala Gly Arg Leu Gly Leu Pro Lys Ala Glu Cys Val Arg Ala Thr Ser
                1045                1050                1055

Cys Thr Ile Ser Trp Arg Gly Val Trp Ser Leu Thr Ser Tyr Lys Glu
            1060                1065                1070

Leu Arg Ser Ile Ile Gly Leu Arg Glu Pro Thr Leu Gln Ile Val Pro
        1075                1080                1085

Ile Leu Ala Leu Arg Gly Ser His Met Asn Trp Thr Arg Phe Asn Gln
    1090                1095                1100

Met Thr Ser Val Met Gly Gly Gly Val Gly
1105                1110

<210> SEQ ID NO 23
<211> LENGTH: 3345
<212> TYPE: DNA
<213> ORGANISM: Bombyx mori R2 element

<400> SEQUENCE: 23
atgatggcga gcaccgcact gtcccttatg ggacggtgta acccggatgg ctgtacacgt      60
ggtaaacacg tgacagcagc cccgatggac ggaccgcgag gaccgtcaag cctagcaggt     120
accttcgggt ggggccttgc gatacctgcg gcgaaccct gtggtcgggt ttgcagcccg      180
gccacagtgg gttttttttcc tgttgcaaaa aagtcaaata agaaaatag acctgaagcc     240 tctggcctcc cgctggagtc agagaggaca ggcgataacc cgactgtgcg gggttccgcc    300
ggcgcagatc ctgtgggtca ggatgcgcct ggttggacct gccagttctg cgaacgaacc    360
ttttcgacca acaggggttt gggtgtccac aagcgtagag cccacccttgt tgagaccaat    420 acggatgccg ctccgatgat ggtgaagcgg cgtggcatg gcgaggaaat cgacctcctc     480
gctcgcaccg aggccaggtt gctcgctgag cggggtcagt gctcgggtgg agacctcttt     540
```

-continued

```
ggcgcgcttc cagggtttgg aagaactctg gaagcgatta agggacaacg gcggagggag    600
ccttatcggg cattggtgca agcgcacctt gcccgatttg gttcccagcc gggtccctcg    660
tcgggggggt gctcggccga gcctgacttc cggcgggctt ctggagctga ggaagcgggc    720
gaggaacgat gcgccgaaga cgccgctgcc tatgatccat ccgcagtcgg tcagatgtcg    780
cccgatgccg ctcgggttct ctccgaactc cttgagggtg cggggagaag acgagcgtgc    840
agggctatga gacccaagac tgcagggcgg cgaaacgatt tgcacgatga tcggacagct    900
agtgcccaca aaaccagtag acaaaagcgc agggcagagt acgcgcgtgt gcaggaactg    960
tacaagaagt gtcgcagcag agcagcagct gaggtgatcg atggcgcgtg tgggggtgtc    1020
ggacactcgc tcgaggagat ggagacctat tggcgaccta tcctcgagag agtgtccgat    1080
gcacctgggc ctacaccgga agctcttcac gccctagggc gtgcggagtg cacgggggc     1140 aatcgcgact acacccagct gtggaagccg atctcggtgg aagagatcaa ggcctcccgc    1200
tttgactggc gaacttcgcc gggcccggac ggtatacgtt cgggtcagtg gcgtgcggtt    1260
cctgtgcact tgaaggcgga aatgttcaat gcatggatgg cacgaggcga aatacccgaa    1320
attctacggc agtgccgaac cgtctttgta cctaaggtgg agagaccagg tggaccgggg    1380
gaatatcgac cgatctcgat cgcgtcgatt cccctgagac actttcactc catcttggcc    1440
cggaggctgt tggcttgctg ccccctgat gcacgacagc gcggatttat ctgcgccgac    1500
ggtacgctgg agaattccgc agtactggac gcggtgcttg gggatagcag gaagaagctg    1560
cgggaatgtc acgtggcggt gctagacttc gccaaggcat ttgacacagt gtctcacgag    1620
gcacttgtcg aattgctgag gttgaggggc atgcccgaac agttctgcgg ctacattgct    1680
cacctatacg atacggcgtc caccaccta gccgtgaaca atgaaatgag cagccctgta    1740
aaagtgggac gaggggttcg tcaagggac cctctgtcgc cgatactctt caacgtggtg    1800
atggacctca tcctggcttc cctgccggag agggtcgggt ataggttgga gatggaactc    1860
gtgtccgctc tggcctatgc tgacgaccta gtcctgcttg cggggtcgaa ggtagggatg    1920
caggagtcca tctctgctgt ggactgtgtc ggtaggcaga tgggcctacg cctgaattgc    1980
aggaaaagcg cggttctgtc tatgataccg gatggccacc gcaagaagca tcactacctg    2040
actgagcgaa ccttcaatat tggaggtaag ccgctcaggc aggtgagttg tgttgagcgg    2100
tggcgatatc ttggtgtcga ttttgaggcc tctggatgcg tgacattaga gcatagtatc    2160
agtagtgctc tgaataacat ctcaagggca cctctcaaac cccaacagag gttggagatt    2220
ttgagagctc atctgattcc gagattccag cacggttttg tgcttggaaa catctcggat    2280
gaccgattga gaatgctcga tgtccaaatc cggaaagcag tcggacagtg gctaaggcta    2340
ccggcggatg tgcccaaggc atattatcac gccgcagttc aggacggcgg cttagcgatc    2400
ccatcggtgc gagcgaccat cccggacctc attgtgaggc gtttcggggg gctcgactcg    2460
tcaccatggt cagtggcaag agccgccgcc aaatctgata agattcgtaa gaaactgcgg    2520
tgggcctgga acagctccg caggttcagc cgtgttgact ccacaacgca acgaccatct    2580
gtgcgcttgt tttggcgaga acatctgcat gcatctgttg atggacgcga acttcgcgaa    2640
tccacacgca ccccgacatc cacaaagtgg attagggagc gatgcgcgca gataaccgga    2700
cgggacttcg tgcagttcgt gcacactcat atcaacgccc tcccatcccg cattcgcgga    2760
tcgagagggc gtagaggtgg gggtgagtct tcgttgacct gccgtgctgg ttgcaaggtt    2820
agggagacga cggctcacat cctacaacag tgtcacagaa cacacggcgg ccggattcta    2880
```

```
cgacacaaca agattgtatc tttcgtggcg aaagccatgg aagagaacaa gtggacggtt    2940
gagctggagc cgaggctacg aacatcggtt ggtctccgta agccggatat tatcgcctcc    3000
agggatggtg tcggagtgat cgtggacgtg caggtggtct cgggccagcg atcgcttgac    3060
gagctccacc gtgagaaacg taataaatac gggaatcacg gggagctggt tgagttggtc    3120
gcaggtagac taggacttcc gaaagctgag tgcgtgcgag ccacttcgtg cacgatatct    3180
tggaggggag tatggagcct gacttcttat aaggagttaa ggtccataat cgggcttcgg    3240
gaaccgacac tacaaatcgt tccgatactg gcgttgagag gttcacacat gaactggacc    3300
aggttcaatc agatgacgtc cgtcatgggg ggcggcgttg gttga                   3345
```

<210> SEQ ID NO 24
<211> LENGTH: 50
<212> TYPE: DNA
<213> ORGANISM: Bombyx mori

<400> SEQUENCE: 24

```
taaacggcgg gagtaactat gactctctta aggtagccaa atgcctcgtc                50
```

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 25

```
ctgcagtaat acgactcact ataggacttg gggaatccga ct                        42
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 26

```
ttttcatcgc cggatcatc                                                  19
```

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 27

```
ggaaacagct atgaccatg                                                  19
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 28

```
gatgacgagg catttggcta                                                 20
```

<210> SEQ ID NO 29
<211> LENGTH: 43
<212> TYPE: DNA
<213> ORGANISM: Artificial Sequence

```
<220> FEATURE:
<223> OTHER INFORMATION: Description of Artificial Sequence:  primer

<400> SEQUENCE: 29
ctgcagtaat acgactcact ataggttgag ccttgcacag tag              43

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence:  primer

<400> SEQUENCE: 30
cgacggccag tgccaagctt gcatgcctgc aggtcgactc tagaggatcc       50

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 31
cgggatccga agccaaggga gcgag                                  25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:  primer

<400> SEQUENCE: 32
gctctagagc gtacggccac gatc                                   24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 33
ggggtaccga caggtttccc gactg                                  25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 34
gctctagagt tcccttggct gtggt                                  25

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence:  primer

<400> SEQUENCE: 35
gctctagagc aagcaagcgc gggtaaacgg cgggagtaac tatgactctc ttaa  54
```

```
<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 36
taatacgact cactatag                                                 18

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 37
aattcaagca agcgcgg                                                  17

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 38
cgttcttcgg ggcgaaaact c                                             21
```